US008930169B2

(12) United States Patent
Adachi et al.

(10) Patent No.: US 8,930,169 B2
(45) Date of Patent: Jan. 6, 2015

(54) CAPACITIVE ULTRASONIC TRANSDUCER AND ENDO CAVITY ULTRASONIC DIAGNOSIS SYSTEM USING THE SAME

(75) Inventors: Hideo Adachi, Iruma (JP); Katsuhiro Wakabayashi, Tokyo (JP); Akiko Mizunuma, Tokyo (JP); Atsushi Osawa, Tokyo (JP); Tatsuo Kaimai, Tokyo (JP); Shinji Yasunaga, Asaka (JP); Kiyoshi Nemoto, Tokyo (JP); Miyuki Murakami, Tokyo (JP); Kousei Tamiya, Sagamihara (JP); Yu Kondo, Yamato (JP)

(73) Assignee: Olympus Corporation, Tokyo (JP)

( * ) Notice: Subject to any disclaimer, the term of this patent is extended or adjusted under 35 U.S.C. 154(b) by 948 days.

(21) Appl. No.: 13/040,922

(22) Filed: Mar. 4, 2011

(65) Prior Publication Data

US 2011/0213592 A1    Sep. 1, 2011

Related U.S. Application Data

(62) Division of application No. 11/666,372, filed as application No. PCT/JP2005/019336 on Oct. 20, 2005, now abandoned.

(30) Foreign Application Priority Data

Oct. 27, 2004 (JP) ................................ 2004-312172
Jan. 21, 2005 (JP) ................................ 2005-014414
Jan. 21, 2005 (JP) ................................ 2005-014415

(51) Int. Cl.
| | | |
|---|---|---|
| *G06F 15/00* | (2006.01) | |
| *A61B 8/14* | (2006.01) | |
| *A61B 8/12* | (2006.01) | |
| *A61B 8/00* | (2006.01) | |
| *B06B 1/02* | (2006.01) | |
| *G10K 9/12* | (2006.01) | |

(52) U.S. Cl.
CPC . *A61B 8/12* (2013.01); *A61B 8/445* (2013.01); *B06B 1/0292* (2013.01); *G10K 9/12* (2013.01); *B06B 2201/76* (2013.01)
USPC ........... 702/191; 600/459; 600/437; 600/439; 600/443

(58) Field of Classification Search
USPC ................... 600/437, 439, 443, 459; 73/635; 702/191
See application file for complete search history.

(56) References Cited

U.S. PATENT DOCUMENTS 5,701,901 A    12/1997  Lum et al.
6,497,667 B1   12/2002  Miller et al.
(Continued)

FOREIGN PATENT DOCUMENTS

| JP | 2005-511115 | 4/2005 |
|---|---|---|
| WO | WO 02/43593 A1 | 6/2002 |
| WO | WO 03/035281 A2 | 5/2003 |

OTHER PUBLICATIONS

Extended Partial European Search Report dated Apr. 27, 2011 from EP 11001279.6-2319.

(Continued)

*Primary Examiner* — Baisakhi Roy
(74) *Attorney, Agent, or Firm* — Scully, Scott, Murphy & Presser, PC

(57) ABSTRACT

A capacitive ultrasonic transducer (c-MUT) comprising a silicon substrate and a transducer element which comprises transducer cells, each of which is constituted by a first electrode equipped on the top surface of the silicon substrate, a second electrode placed opposite to the first electrode with a predetermined gap therefrom and a membrane for supporting the second electrode, wherein a trench is equipped between the adjacent transducers and a conductive film is formed in the trench.

2 Claims, 30 Drawing Sheets

(56) References Cited

U.S. PATENT DOCUMENTS

| | | |
|---|---|---|
| 6,511,427 B1 | 1/2003 | Sliwa, Jr. et al. |
| 6,645,145 B1 | 11/2003 | Dreschel et al. |
| 7,360,427 B2* | 4/2008 | Drinkwater et al. ............ 73/635 |
| 7,728,490 B2 | 6/2010 | Adachi et al. |
| 7,800,189 B2 | 9/2010 | Caliano et al. |
| 8,162,835 B2* | 4/2012 | Ichikawa et al. .............. 600/443 |
| 2003/0158479 A1* | 8/2003 | Li et al. .......................... 600/437 |
| 2005/0197577 A1* | 9/2005 | Makin et al. ................... 600/439 |
| 2007/0167811 A1* | 7/2007 | Lemmerhirt et al. ......... 600/459 |

OTHER PUBLICATIONS

Official Action dated Dec. 7, 2010 received from the Japanese Patent Office.

Mills D.M., "Medical Imaging With Capacitive Micromachined Ultrasound Transducer (cMUT) Arrays", *IEEE Ultrasonics Symposium* pp. 384-390 (2004).

Supplementary European Search Report dated Oct. 13, 2010.

Jin X. et al., "Characterization of One-Dimensional Capacitive Micromachined Ultrasonic Immersion Transducer Arrays", *IEEE Transactions on Ultrasonic, Ferroelectrics and Frequency Control* 48(3):750-760 (2001).

Bashford A.G. et al., "Micromachined Ultrasonic Capacitance Transducers for Immersion Applications", *IEEE Transactions on Ultrasonic, Ferroelectrics and Frequency Control* 45(2):367-375 (1998).

Huang Y. et al., "Fabricating Capacitive Micromachined Ultrasonic Transducers With Wafer-Bonding Technology", *Journal of Microelectromechanical Systems* 12(2):128-137 (2003).

Demirci U. et al., "Forward-Viewing CMUT Arrays for Medical Imaging", IEEE Transactions on Ultrasonics, Ferroelectrics, and Frequency Control 51(7):886-894 (2004).

Mills D.M. et al., "Real-Time In-Vivo Imaging With Capacitive Micromachined Ultrasound Transducer (cMUT) Linear Arrays", *IEEE Ultrasonics Symposium* pp. 568-571 (2003).

Office Action dated Jan. 11, 2011 received in U.S. Appl. No. 11/666,372.

* cited by examiner

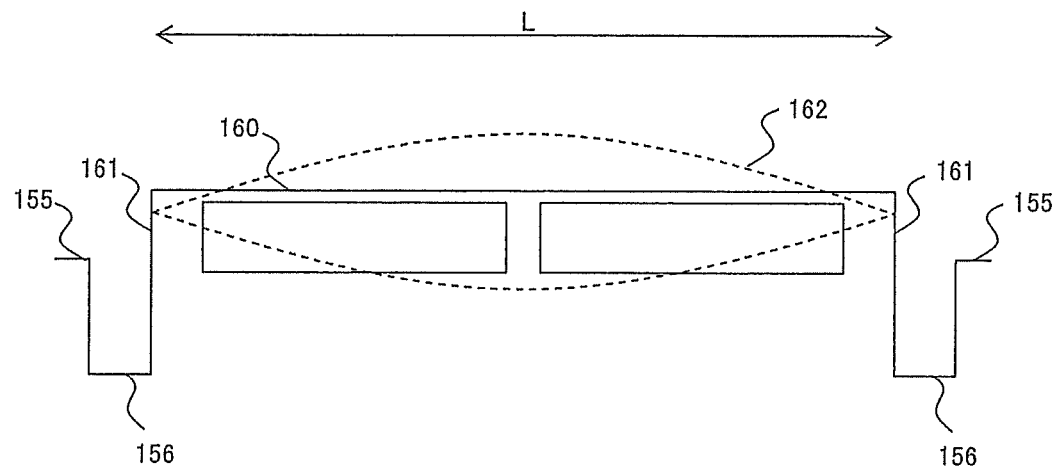
F I G. 2

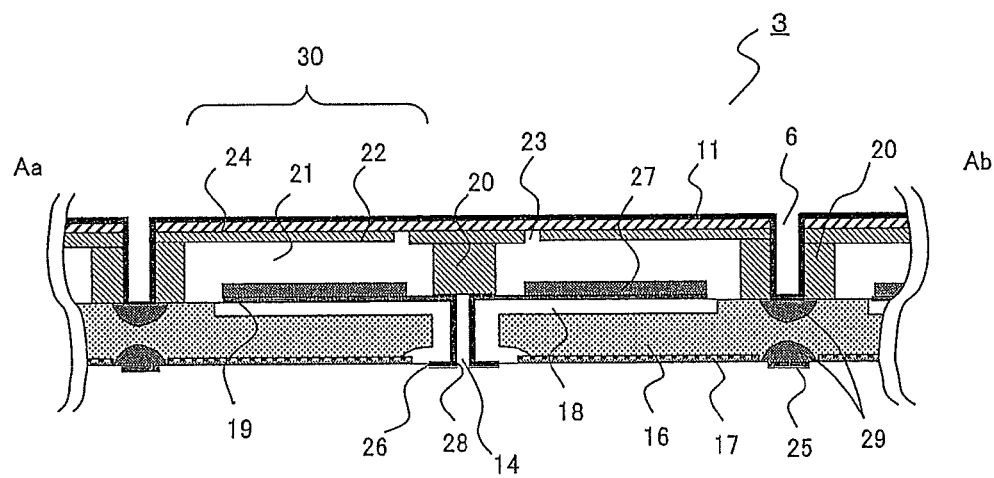
F I G. 6

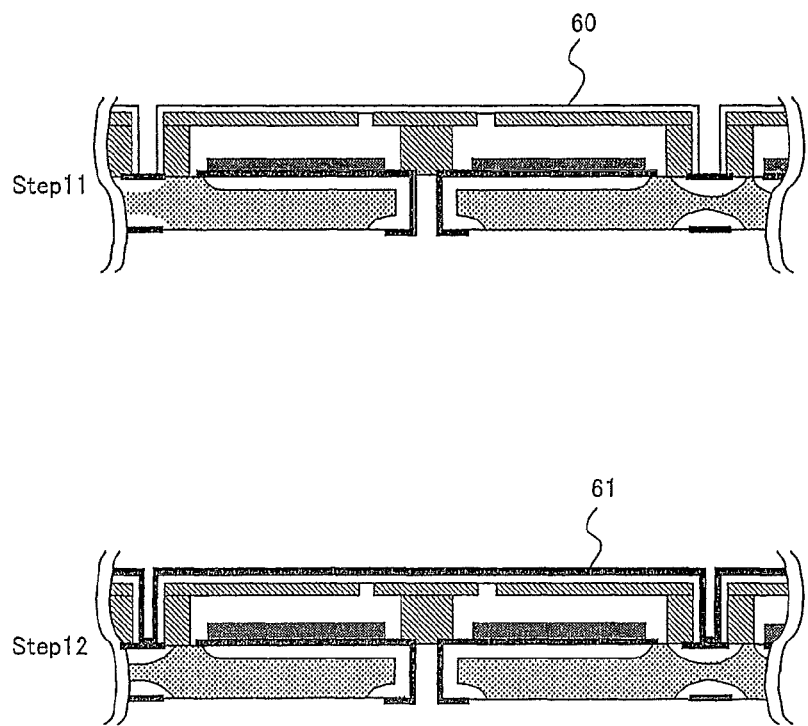
F I G. 7C

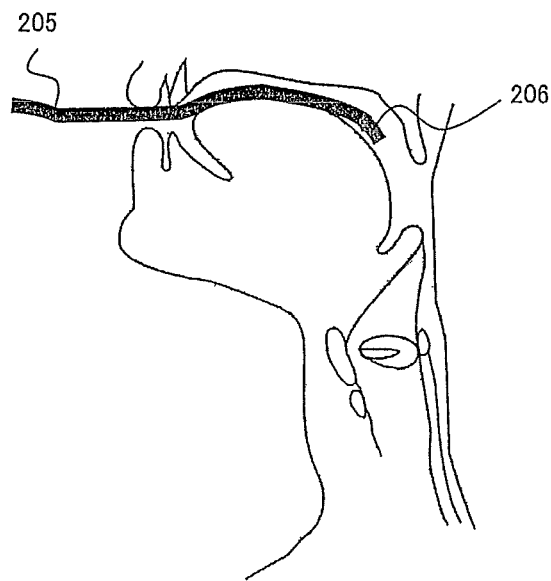
F I G. 2 1 A

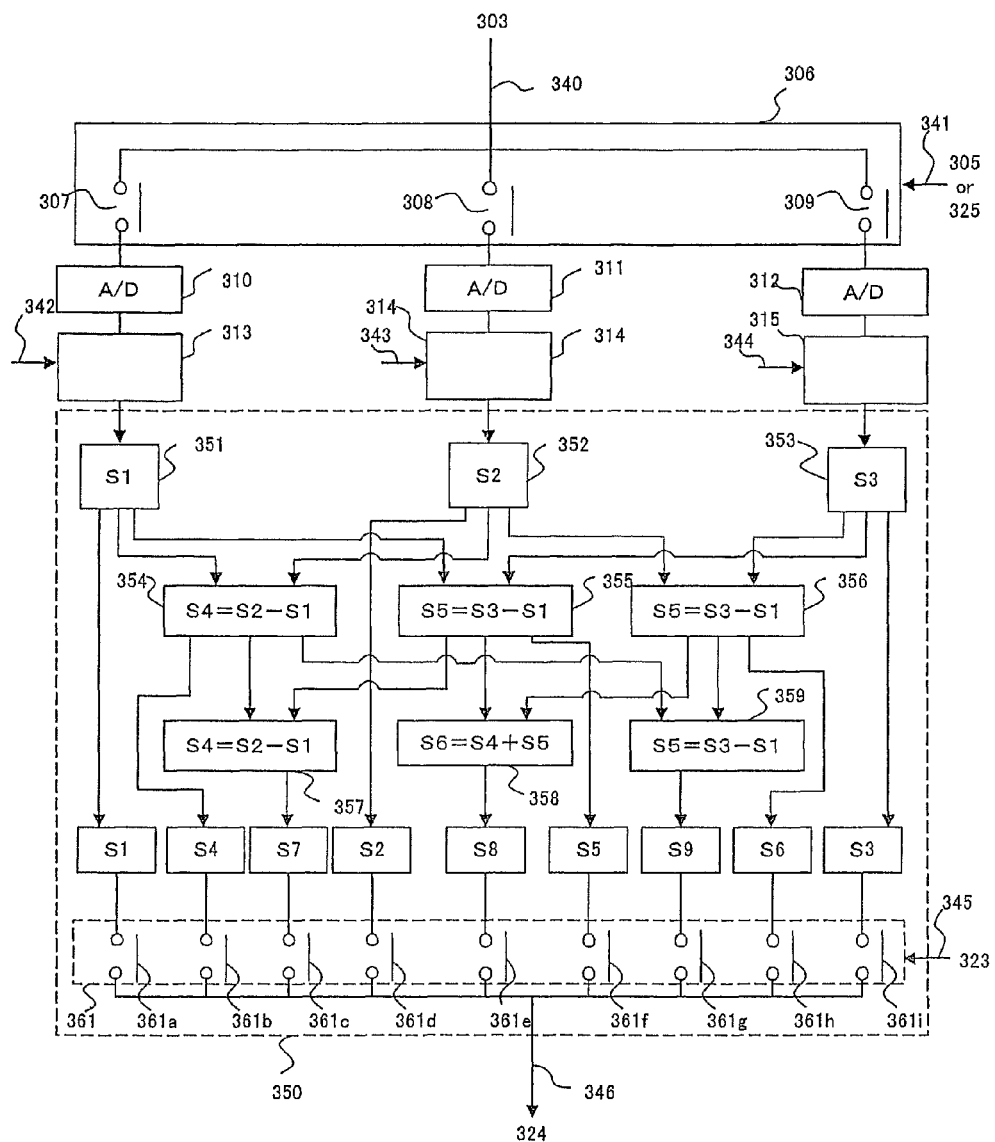
F I G. 2 5

US 8,930,169 B2

CAPACITIVE ULTRASONIC TRANSDUCER AND ENDO CAVITY ULTRASONIC DIAGNOSIS SYSTEM USING THE SAME

CROSS REFERENCE TO RELATED APPLICATIONS

The present application is a divisional of copending application Ser. No. 11/666,372 filed Jul. 11, 2007, which is a national stage application under 35 U.S.C. §371 of International Application Serial No. PCT/JP2005/019336 filed Oct. 20, 2005, which claims benefit of Japanese Patent Application No. 2004-312172 filed Oct. 27, 2004, Japanese Patent Application No. 2005-014414 filed Jan. 21, 2005 and Japanese Patent Application No. 2005-014415 filed Jan. 21, 2005, the entire contents of which are incorporated herein by reference.

TECHNICAL FIELD

The present invention relates to a capacitive micromachined ultrasonic transducer (c-MUT) produced using silicon process and an endoscopic ultrasonic diagnostic system including c-MUT.

BACKGROUND ART

An ultrasonic diagnosis method for transmitting an ultrasound to an endo cavity wall and diagnosing by imaging the body tissue using an echo signal from body tissue targets has become widely used. One of the equipment used for the ultrasonic diagnosis method is an ultrasonic endoscope. The ultrasonic endoscope is equipped with an ultrasonic transducer at the head part of an insertion tube which is for inserting into an endo cavity. The transducer is configured to transmit an ultrasound into an endo cavity by converting an electric signal into an ultrasound, receive an ultrasound which is reflected from the body tissue and convert it into an electric signal.

A conventional ultrasonic transducer has been using a ceramic lead zirconate titanate (PZT) as a piezoelectric element for converting an electric signal into an ultrasound. However, attention is recently focused on a capacitive micromachined ultrasonic transducer (abbreviated as "c-MUT" hereinafter) produced by processing a silicon semiconductor substrate by means of a silicon micromachining technique. This is one of devices generally called a micromachine (i.e., Micro Electro-Mechanical System: MEMS).

A MEMS device is formed on a silicon substrate or glass substrate as a miniature structure which is an electrically and mechanically combined component sometimes accompanied with driving integral circuit, such as a transducer for outputting a mechanical force, a driving mechanism for driving the transducer and a semiconductor integrated circuit for controlling the driving mechanism. The basic characteristic of the MEMS device lies in integrating the transducer, which is configured as a mechanical structure, of a part of the device, and driving the transducer electrically by applying a Coulomb attraction between electrodes.

Meanwhile, a non-patent document 1 has disclosed a c-MUT as shown in FIG. 1. FIG. 1 (*a*) shows the top face of two sets of a single-dimensional c-MUT array consisting of 64 pieces of elements; FIG. 1 (*b*) shows a singularized one piece of c-MUT element equipped with dummy neighbors; and FIG. 1 (*c*) shows an enlarged diagram of a c-MUT element structured by parallelly connected by 8×160 pieces of cells.

The c-MUT element 150 comprises a plurality of cells 151, upper electrodes 152 equipped on the upper parts of individual cells, ground electrodes 153, dummy neighbors 155 and trenches 156. The upper electrodes 152 are connected to one another and they are connected to the electrodes 153 on the ends. The dummy neighbors 155 are for preventing a crosstalk with the adjacent elements. A trench 156 is equipped between the electrode 153 and dummy neighbor 155.

The upper electrodes are supported by a membrane. Bottom electrodes (not shown herein) are equipped at a position opposite to the upper electrodes 152 within the cells, and there is a cavity between the bottom electrode and the membrane.

As a voltage is applied to the upper and bottom electrodes of the element, each cell is simultaneously driven to vibrate concurrently in the same phase, thereby transmitting an ultrasound.

The non-patent document 1 documents a finding that a Lamb wave (i.e., A0 mode) and a Stoneley wave (i.e., a boundary wave) transmitting between the solid phase and fluid phase give a great influence on a crosstalk between the elements.

FIG. 2 shows a vibrational wave occurring in a membrane 160 in the case of generating an ultrasound by using the c-MUT shown in FIG. 1. FIG. 2 is a cross-sectional diagram of the element shown in FIG. 1. If there are distinctive end parts 161 by equipping the trenches 156 on both ends, as in the element 150, a standing wave 162 is generated with the end parts 161 as nodes.

That is, a standing wave is generated between a pair of walls existing apart from each other by a frequency which is determined by the distance between the walls and by the transverse sonic velocity of a material (i.e., silicon in the configuration of FIG. 2) filling therebetween. Considering a pair of adjacent trenches, an vibrational wave excited on a membrane is first transmitted along the surface of the membrane as a Lamb wave or Stoneley wave. Then an ultrasound, that is the vibrational wave, is multiply reflected by the right side wall on the left side trench and left side wall of the right side trench, becoming possibly a transverse standing wave. The transverse standing wave becomes an vibrational wave with a base having a frequency component of which a distance L is ½λ overlapped with a high-order standing wave of the base. Therefore, the existence of such a pair of walls generates a standing wave. The standing wave 162 is possible to become a noise component in an transducing of an ultrasound.

Non-patent document 1: Xuecheng Jin, et al (3), "Characterization of One-Dimensional Capacitive Micromachined Ultrasonic Immersion Transducer Arrays", in "IEEE Transactions on Ultrasonic, Ferroelectrics and Frequency Control", Vol. 48, NO. 3, P750-760, May 2001

Non-patent document 2: A. G. Bashford, et al (2), "Micromachined Ultrasonic Capacitance Transducers for Immersion Applications", in "IEEE Transactions on Ultrasonic, Ferroelectrics and Frequency Control", Vol. 45, No. 2, March (1998), P. 367-375

DISCLOSURE OF INVENTION

A capacitive ultrasonic transducer (c-MUT) according to the present invention is one comprising a silicon substrate and a transducer element which comprises transducer cells, each of which is constituted by a first electrode equipped on the top surface of the silicon substrate, a second electrode placed opposite to the first electrode with a predetermined gap therefrom and a membrane for supporting the second electrode, wherein a trench is equipped between the adjacent transducer elements and a conductive film is formed in the trench.

A production method for a c-MUT comprising a silicon substrate and a transducer element which comprises transducer cells, each of which is constituted by a first electrode equipped on the top surface of the silicon substrate, a second electrode placed opposite to the first electrode with a predetermined gap therefrom and a membrane for supporting the second electrode according to the present invention comprises: a trench forming process for equipping in between the adjacent transducer elements with a trench; and a conductivity forming process for forming a third electrode on a bottom of the trench by making it conductive.

An endo cavity ultrasonic endoscopic diagnosis system according to the present invention comprises: an ultrasonic endoscopic scope equipped with a c-MUT for transmitting and receiving an ultrasound; a transducer state discernment unit for discerning such a wrong state of the c-MUT as an electrical short; and an image construction unit for constructing an ultrasonic diagnosis image from sensed information sensed by the c-MUT according to the state discerned by the transducer state discernment unit.

An endo cavity ultrasonic endoscopic diagnosis system according to the present invention comprises: an ultrasonic endoscope equipped with a c-MUT for transmitting and receiving an ultrasound; a transducer state discernment unit for discerning a state of the c-MUT; a storage unit for storing information sensed by the c-MUT; a storage control unit for having the storage unit, which corresponds to a discernment result, store the information based on the discernment result by the transducer state discernment unit; an arithmetic operation unit for performing an arithmetic operation process based on at least one piece of the information among the information stored in the storage unit; and an image construction unit for constructing an ultrasonic diagnosis image from an arithmetic operation result of the operation process performed by the arithmetic operation unit.

A noise elimination apparatus for eliminating a noise component from information sensed by a c-MUT used for an endo cavity ultrasonic endoscopic diagnosis system comprising an ultrasonic endoscopic scope equipped with the c-MUT for transmitting and receiving an ultrasound according to the present invention comprises: a first storage unit for storing the first information sensed by making the c-MUT transmit an ultrasound under a condition of the ultrasound not reflecting; a second storage unit for storing the second information sensed by the c-MUT transmitting and receiving an ultrasound under a condition thereof in a state of being in the inside of an endo cavity and yet not touching an inside wall thereof; and an arithmetic operation unit for calculating a correlation or difference between the second information and first information.

BRIEF DESCRIPTION OF DRAWINGS

FIG. 2 is a diagram showing a situation of generating a standing wave in a membrane in the case of using the c-MUT shown in FIG. 1;
FIG. 6 is a diagram of cross-section Aa-Ab of FIG. 5;
FIG. 7C is a diagram showing a production process of a c-MUT according to the first-1 embodiment (part 3);
FIG. 21A is a diagram showing the case of inserting, into an endo cavity (i.e., in the state of inserting into a mouth), an ultrasonic transducer according to the second embodiment;
FIG. 25 is a diagram showing an arithmetic operation control circuit for performing a signal process of a plurality of patterns according to a fourth embodiment.

BEST MODE FOR CARRYING OUT THE INVENTION

Figure 1:
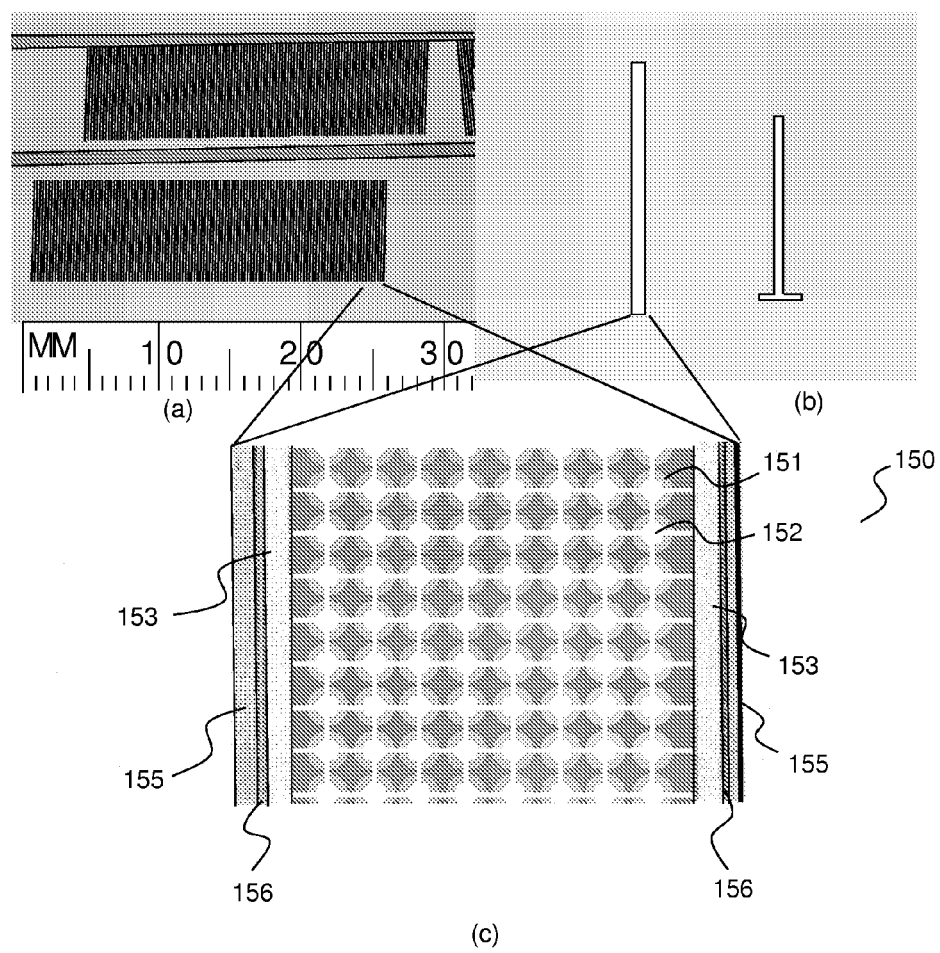
FIG. 1 is a diagram showing a conventional c-MUT.

However, the equipment of the trench 156, dummy neighbor 155 and electrode zone 153 between the trench 156 and cell zone for transmitting and receiving an ultrasound, as in the transducer element 150, makes a ratio of the transducer zone to the entirety of the transducer element small.

If the area size of the cell zone is desired to maintain at a certain size in this case, the transducer element needs to be enlarged, resulting in negating a possibility of miniaturizing an ultrasonic transducer employing the c-MUT. If the size of the element is attempted to maintain a similar size as before, on the other hand, requiring the area size of the cell zone to be smaller, resulting in decreasing a generated output of ultrasounds.

A preferred embodiment of the present invention is to provide a c-MUT not allowing a decrease of an area size ratio of a cell zone to the entirety of the c-MUT equipped with trenches respectively on both ends of a transducer element, and a reduced output of a generated ultrasound.

Incidentally, if a conventional piezoelectric transducer is operated in the air, there is a possibility of a breakdown or rapid deterioration of a characteristic occurring, and therefore an operation in the air has been avoided. This has conventionally limited a use of the ultrasonic endoscopic scope only in the state of contacting with an inside wall of an endo cavity. Likewise, it is unable to transmit an ultrasound in the air, hence precluding a detection of a noise signal stemming only from a transducer.

Also, a detection of an aerial sonic wave has been conventionally impossible by the same structure as a piezoelectric transducer of a type to be contacting with an endo cavity wall because there is a large difference in acoustic impedance between a live tissue and air.

Due to this, there has not conventionally been necessary to detect information related to a state of an ultrasonic transducer as to whether or not it contacts with an endo cavity wall.

In the case of using an ultrasonic transducer capable of transmitting and receiving an ultrasound (called as "aerial ultrasound") in the state of the ultrasonic transducer not touching with an endo cavity wall, however, a detection of information related to a state of whether or not the ultrasonic transducer touching an endo cavity wall becomes necessary.

A preferred embodiment of the present invention accordingly provides an endo cavity ultrasonic diagnosis system which detects information related to a state of whether or not the ultrasonic transducer touching an endo cavity wall.

Meanwhile, there has conventionally been no endo cavity ultrasonic diagnosis system existing to obtain an ultrasonic diagnosis image which is picked up with an ultrasonic transducer touching an endo cavity wall and one which is picked up with the transducer not touching the endo cavity wall by using the same transducer.

Next, the technique disclosed in the non-patent document 1 equips trenches respectively on both ends of a transducer element, thereby suppressing a crosstalk between elements, as noted above. The equipment of such trenches, however, has been faced with the problem of generating a noise caused by a standing wave when using an element equipped with the trenches respectively on both ends as described for FIG. 2.

Another preferred embodiment of the present invention accordingly provides an endo cavity ultrasonic diagnosis system which builds up an ultrasonic diagnosis image related to an asperity of an endo cavity wall while inserting, into the endo cavity, an ultrasonic endoscopic scope equipped with the same c-MUT regardless of it contacting the endo cavity wall, and which also builds up an ultrasonic diagnosis image related to a fault by being stationary held in contact with the endo cavity wall when reaching a diagnosis region, with a noise component being removed from the thusly buildup ultrasonic diagnosis images.

Now, the following is a description on the preferred embodiment of the present invention.

First Embodiment

The First-1 Embodiment

The present embodiment describes a production of a transducer element equipped with a ground electrode on the bottom of a trench.

Figure 3:
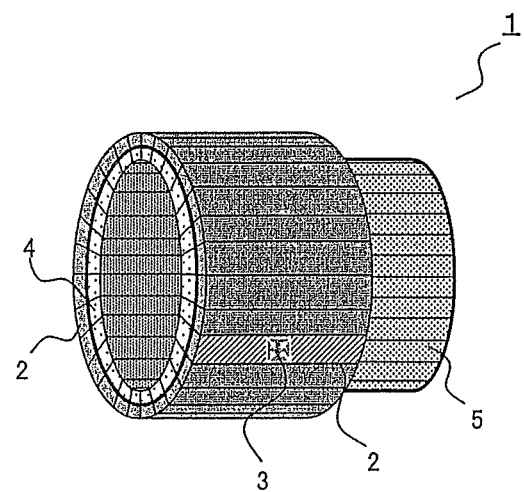
FIG. 3 is a diagram showing a radial scanning ultrasonic transducer according to a first-1 embodiment.

FIG. 3 shows a capacitive radial scanning array ultrasonic transducer according to the present embodiment. The radial scanning ultrasonic transducer 1 comprises a transducer unit 2 constituted by a plurality of transducer elements 3, by a control circuit unit 4 and by a flexible print circuit board (FPC) 5 for interconnection.

A plurality of rectangular transducer units 2 is serially connected in a short direction thereof, resulting in featuring a cylindrical form. The FPC 5 is featured with a wiring pattern and electrode pads on the FPC. The control circuit unit 4 is placed, as one control circuit for one transducer unit, on the reverse side of the c-MUT vis-à-vis the FPC 5 and in equiposition with the transducer unit 2. The control circuit unit 4, being equipped on the rear surface of the transducer unit 2 (i.e., on the internal circumference of the cylindrical form), is configured for controlling an exchange of electrical signals to and from the transducer units 2. A through hole penetrating the FPC is featured for an element of the c-MUT as unit, and is placed so as to connect the c-MUT unit to control circuit unit via the through hole. The control circuit unit 4 is constituted by an integrated circuit such as a pulser, charge amplifier and multiplexer, or by such component. Note that the form of the transducer unit 2 is not limited to a rectangle.

Figure 4:
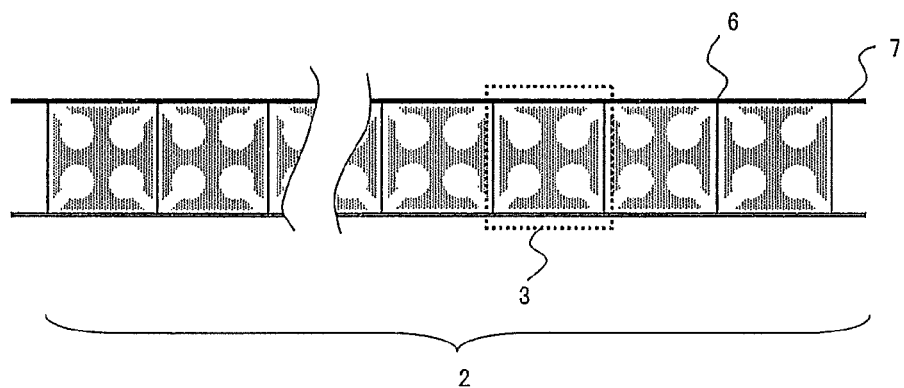
FIG. 4 is a diagram showing a top view of a single body of a transducer unit according to the first-1 embodiment.

FIG. 4 shows a top view of a single body of the transducer unit 2 according to the present embodiment. The transducer unit 2 is constituted by a plurality of square transducer elements 3. The transducer unit 2 shown in FIG. 4 is configured by arraying a plurality of transducer elements 3 in one dimension. In between the adjacent transducer units is featured with a trench 7 (i.e., trench formed along an array direction of transducer unit) penetrating until the FPC 5 vertically to the array direction of transducer units. Also, in between the adjacent transducer elements within each transducer unit is featured with a trench 6 separating transducer elements of a depth of approximately halfway of a silicon substrate 16. Incidentally, a feature of the transducer element is not limited to a square.

Figure 5:
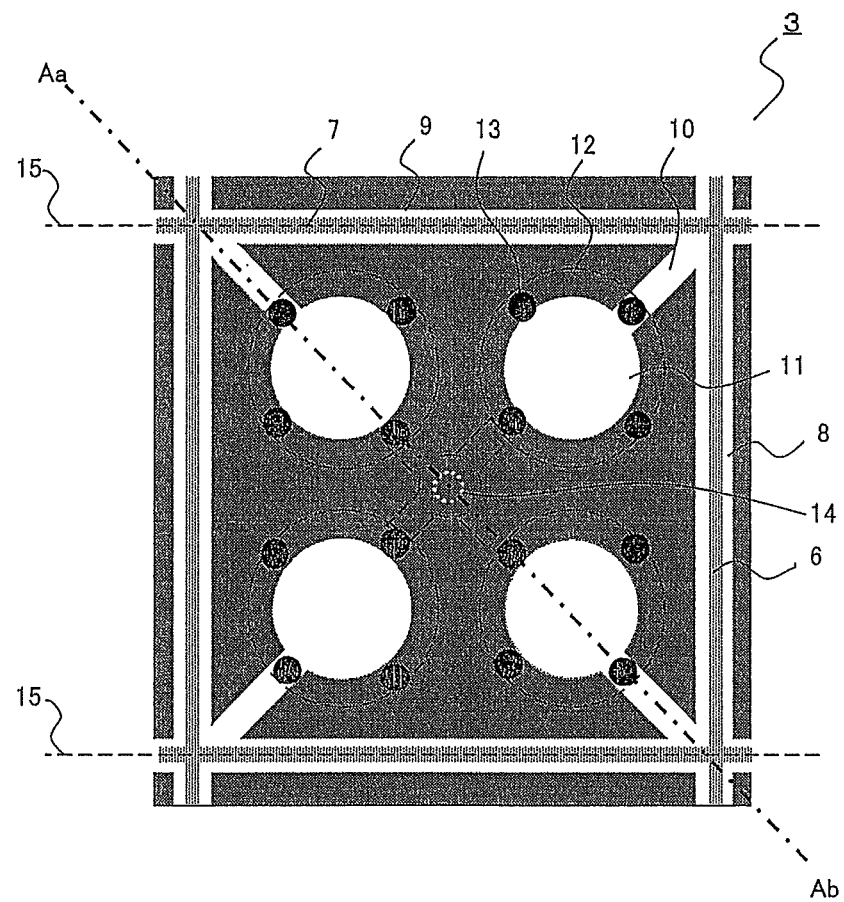
FIG. 5 is a diagram showing a top view of a single body of a transducer element according to the first-1 embodiment.

FIG. 5 shows a top view of a single body of the transducer element 3 according to the present embodiment. The transducer element 3 comprises trenches 7, trenches 6, interconnection combining transducer electrodes 8, 9 and 10, a transducer cell's upper electrode 11, a sacrifice layer material removal hole 13 and a through-hole electrode 14 from a bottom electrode. The back surface (in the direction vertical to the drawing) of the transducer cell's upper electrode 11 is featured with a cavity which is indicated as a cavity periphery part 12.

The transducer element 3 is constituted by a plurality of transducer cells, of which the number thereof is equal to the number of cavities. FIG. 5 shows a configuration of four transducer cells. The numerical 15 shows a dicing line for separating the units.

FIG. 6 is a diagram of cross-section Aa-Ab of FIG. 5. Referring to the cross section, a constituent unit indicated by the numerical 30 is called a transducer cell of the transducer element 3 as noted above. A film covering the upper part of the transducer cell 30 is called a membrane which is a film constituted by the upper electrode 11, upper layer 24 above membrane and under layer 22 beneath membrane in the configuration shown in FIG. 6. The membrane is an vibrating film fixed by members supporting membrane 20 on both ends of each transducer cell. A bottom electrode 19 is structured on the surface of a silicon substrate 16 (at the bottom of a concave part) between the members supporting membrane 20 in a manner to be opposite to the upper electrode 11, and the bottom electrode 19 is covered over with a dielectric film 27 (e.g., $SiO_2$, $Si_3N_4$, $Ta_2O_5$, $BaTiO_3$, $SrTiO_3$, AlN and such).

The bottom electrode 19 is equipped with the through-hole electrode 14 from bottom electrode for electrically connecting the bottom electrode 19 to a electrode pad 26 as signal input-output terminal which is equipped on the bottom face of the silicon substrate 16. Specifically, the bottom electrode 19 is electrically continuous with the electrode pad 26 as signal input-output terminal by way of an interconnection 28 featured on the hole surface of the through-hole electrode 14.

The bottom surface of the silicon substrate 16 is covered with a silicon oxide film 17. The upper electrode 11 and interconnection combining transducer electrodes 10 are constituted by a metallic film of Au, Al, Pt, Ta, Mo, W or such. The upper electrode 11 is electrically continuous with a metallic film covering the side and bottom surfaces of the trenches 6 and 7.

A ground electrode pad 25 is one for making the bottom surface of the silicon substrate 16 electrically continuous with an electrode featured on the bottom surface of the trenches 6 and 7 for connecting the upper electrode 11 to the ground (GND).

The dielectric film 27 is for amplifying a capacitance between the upper electrode 11 and bottom electrode 19 which sandwich a cavity. A depletion layer 18 is one in a state of an electron or electron hole hardly existing, and there is a case of reducing a capacity possessed by a depletion layer, that is reducing a parasitic capacitance by applying a reverse bias.

Note that a cavity (i.e., an air gap) 21 is a space surrounded by the membrane, member supporting membrane 20, bottom electrode 19 and dielectric film 27. Incidentally, a sacrifice layer is formed in the cavity in terms of the production process and a under layer beneath membrane 22 ($Si_3N_4$) is equipped with a sacrifice layer removal hole 23 for removing the sacrifice layer followed by removing the sacrifice layer from the hole when forming the cavity 21.

A "contact resistance" between the ground electrode pad 25 and electrode featured on the bottom of the trenches 6 and 7 is configured to be minimally small (i.e., an ohmic contact). The numerical 29 shows a diffusion region.

Describing on an operation of the transducer cell 30, an application of a voltage to a pair of electrodes of the upper electrode 11 and bottom electrode 19 makes the electrodes mutually pull each other, followed by reverting back to the original state when reducing the voltage to zero. This movement causes the membrane to vibrate, resulting in generating an ultrasound and transmitting it to the upward direction of the upper electrode 11.

Figure 7A:
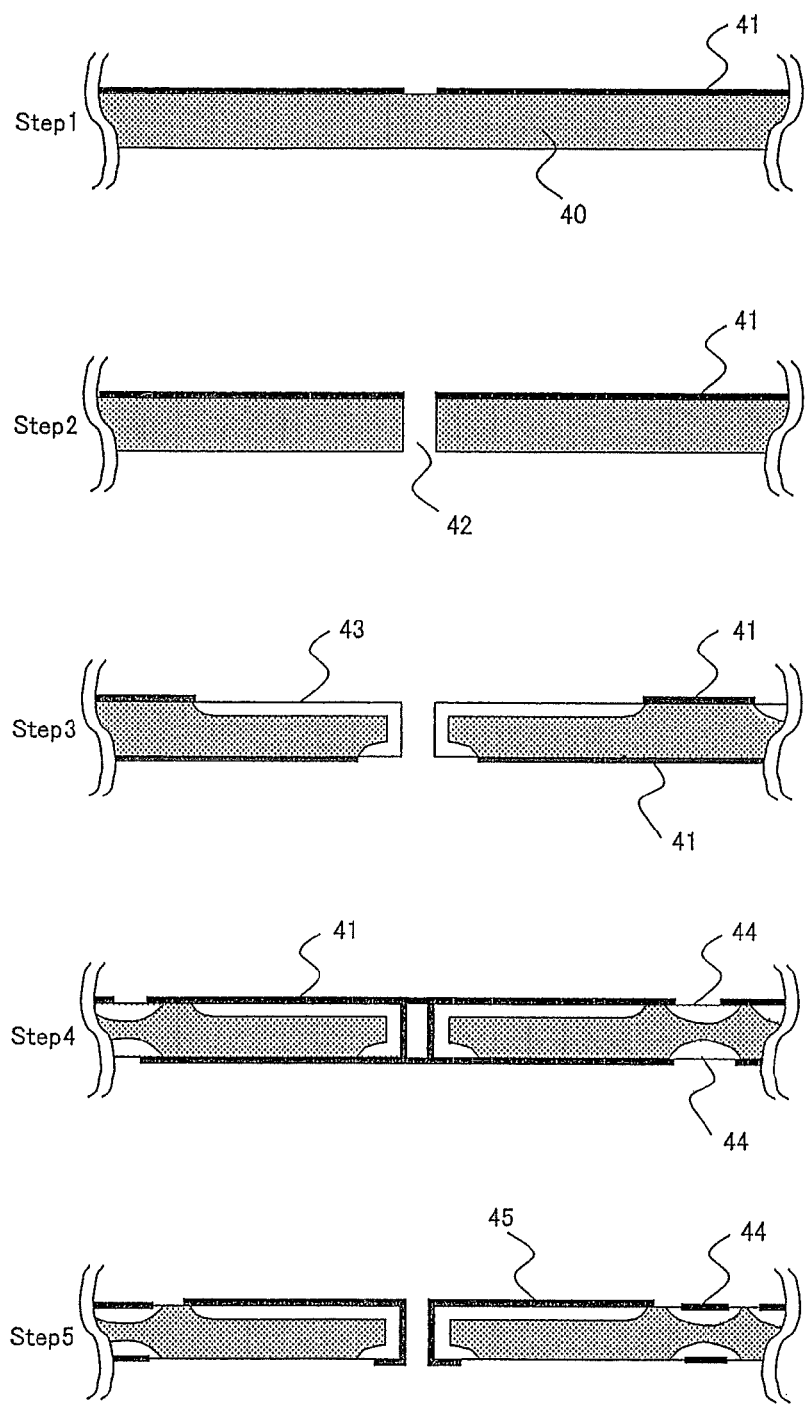
FIG. 7A is a diagram showing a production process of a c-MUT according to the first-1 embodiment (part 1)
Figure 7B:
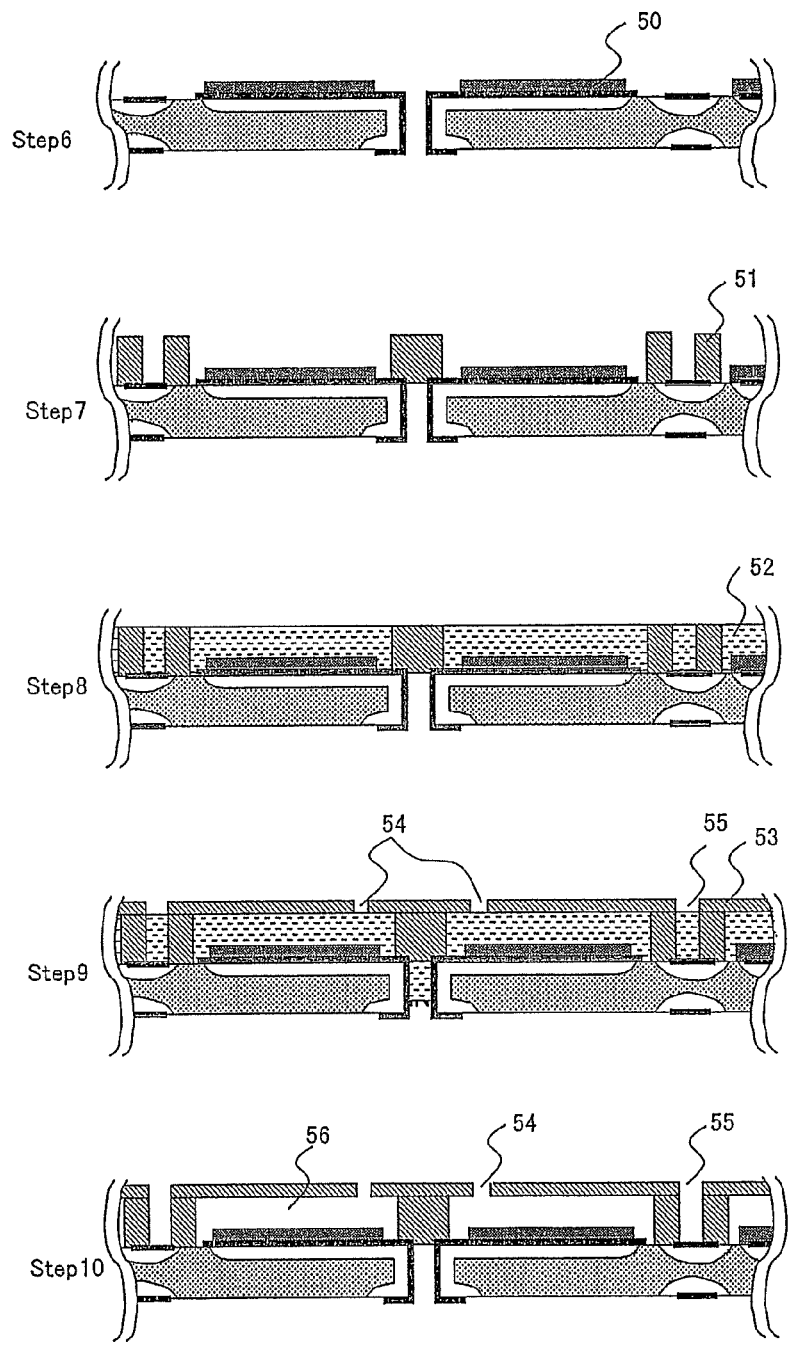
FIG. 7B is a diagram showing a production process of a c-MUT according to the first-1 embodiment (part 2)

Next is a description of a production process of the c-MUT according to the present embodiment by referring to FIG. 7 (i.e., FIGS. 7A, 7B and 7C).

First, the top surface of an N type silicon substrate 40 (of a thickness of 100 through 500 micrometers) is masked by an oxide film ($SiO_2$) 41 (step 1). The mask forming forms an oxide film of a thickness of 3000 to 4000 angstroms for example by a Wet oxidization method. This is followed by a photolithography process applying a patterning for featuring a through-hole 42 for through-hole electrode from bottom electrode and by an etching process removing the patterned oxide film.

Next is to apply an Inductively Coupled Plasma-Reactive Ion Etching (ICP-RIE), thereby penetrating a through-hole 42 where it is not masked in the step 1 (step 2).

Next is to form the depletion layer 43 (step 3). First is to mask the bottom surface of the N type silicon substrate 40 with an oxide film ($SiO_2$), followed by applying a patterning to the top and bottom surfaces of the N type silicon substrate 40 for forming the depletion layer 43 in a photolithography process and removing the oxide film patterned in the etching process. It is then followed by doping a P type ion (Dope (P+)) and applying a heat treatment, thereby forming a P type diffused layer.

The next is to form a contact layer (N+) 44 on both surfaces (step 4). The mask forming process, photolithography process and etching process mask other than a part for forming a contact layer 44 with $SiO_2$. It is followed by doping an N type ion (Dope (N+)) to the unmasked part, and applying a heat treatment, thereby forming an N type diffusing layer. This is applied to the contact layers (N+) 44 of both surfaces of the silicon substrate.

The next is to form an electrode film (Pt/Ti) 45 on both surfaces (step 5). The first is to remove the mask 41, and mask a part other than that part for forming an electrode film with a resist material, followed by forming an electrode film 45 by means of a sputtering and removing the resist material masked in the liftoff process. Note that a material of the electrodes may be Au/Cr, Mo, W, phosphor bronze, Al or such, in lieu of being limited to Pt/Ti.

The next is to form a dielectric film (step 6). The dielectric film (e.g., $SrTiO_3$) 50 is formed by being subjected to the mask forming process, sputtering process and liftoff process. Note that the dielectric film 50 may use a material having a high dielectric constant, such as barium titanate $BaTiO_3$, barium-strontium titanate, tantrum pentoxide, niobium oxide-stabilized tantrum pentoxide, aluminum oxide or titanium oxide $TiO_2$, in lieu of the material being limited to $SrTiO_3$.

The next is to form a layer for supporting membrane (step 7). The application of a mask to a part other than ones for forming the member supporting membrane is followed by a chemical vapor deposition (CVD) forming an SiN layer and removing the mask, thus resulting in forming the member supporting membrane formed by the SiN.

The next fills in between the member supporting membrane formed in the step 7 with a polysilicon 52 as the sacrifice layer (step 8). Note that a material for the sacrifice layer may use a material allowing an etching, such as $SiO_2$ in lieu of being limited to a material such as polysilicon which is used for the present embodiment.

The next forms a under layer beneath membrane 22 (step 9). The first step masks a part becoming a hole 54 for etching out of sacrifice layer material and trench 55, followed by the CVD forming an SiN film 53 and removing the mask. This results in forming the membrane 53 formed by the SiN, the hole 54 and the trench 55.

The next removes the sacrifice layer 52 by means of an etching (step 10). Since the present embodiment is configured to use a polysilicon for the sacrifice layer, the etching is carried out by using $XeF_2$ as an etching agent for removing the sacrifice layer (of polysilicon) from the hole 54 for etching out of sacrifice layer material. This results in forming the cavity 56 and trench 55.

The next closes the hole 54 for etching out of sacrifice layer material (step 11). First masks the bottom (i.e., a contact electrode) of the trench 55 and forms an SiN film on the entirety of the top surface of the element by means of the CVD. It is followed by removing the mask to expose the bottom (i.e., the contact electrode) of the trench 55.

The last step masks parts other than interconnection combining transducer electrodes 8, 9 and 10, transducer cell's upper electrode 11, bottom electrode of the trench 7, and bottom electrode of the trench 6, and forms an electrode film (Pt/Ti) 61 on the entire top face of the transducer element by subjecting to the sputtering and liftoff (step 12), thereby completing the transducer element 3 as shown in FIG. 5.

Note that the forming of the electrode film (and the contact layer), that is, the process for forming the electrode in the trench (i.e., the process for making it conductive) is carried out by means of an ion implantation or CVD and a diffusion process, or a physical vapor deposition (PVD), according to the present embodiment.

As described above, the forming of the ground electrode in the trench eliminates a necessity of equipping a separate zone for a ground electrode within the transducer element and prevents a reduction of the area size ratio of an ultrasound output zone to the transducer element. Also, the equipment of the trench enables a suppression of an influence of a crosstalk between the adjacent elements.

Note that the present embodiment exemplifies a radial type c-MUT; the present invention, however, may also be applied to a convex type, linear type or sector type c-MUT, in lieu of being limited to the present embodiment.

First-2 Embodiment

Described for the present embodiment is a variation of a form of the trench featured in a transducer element.

Figure 8:
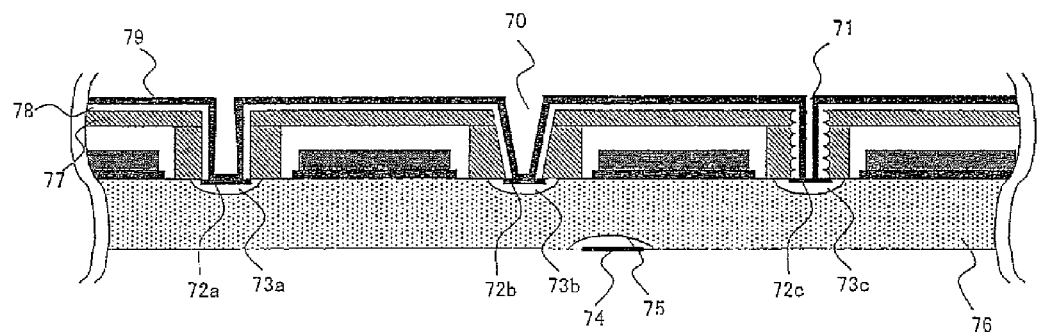
FIG. 8 is a diagram exemplifying a variation of a trench form according to the first-2 embodiment (part 1)

FIG. 8 exemplifies a variation of a trench form according to the present embodiment (part 1). The numerical 70 and 71 indicate trenches. The numerical 76 indicates a silicone substrate. The numerical 72 (i.e., 72a, 72b and 72c) indicate contact electrodes on the top face side of the silicone substrate 76. The numerical 73 (i.e., 73a, 73b and 73c) indicate contact layers featured in the neighborhood of the contact electrodes 72 (i.e., 72a, 72b and 72c). The numerical 74 indicates a contact electrode on the lower face side of the silicon substrate 76. The numerical 75 indicates a contact layer featured in the neighborhood of the contact electrode 74. The numerical 77 and 78 indicate SiN layers. The numerical 79 indicates an electrode film.

The numerical 70 indicates the case of widening the opening part wider than the bottom by forming the trench in a taper form. Such configuration enables a use of a sputtering for forming a film on an electrode. Also enabled is a forming of a thicker film as a result of an easy attachment of an electrode film by means of a sputtering as compared to the case of the side face of a trench being perpendicular. This improves a reliability of wiring.

The numerical 71 indicates the case of forming an irregular surface on the surface of the trench side surface by means of Bosh process. The Bosh process is one for repeating an etching and a passivation (for providing a surface with protective film so as not to occur a chemical reaction) processes alternately by using $C_4F_8$ and $SF_6$ as reaction gases. It enables a process of a high aspect ratio. In the case of forming a trench by the Bosh process, a change of timing between the passivation and etching makes it possible to form a taper and an irregularity.

A common Bosh process is capable of forming a wavy irregularity in the order of ones to tens nanometers. The present embodiment, however, is configured to form an irregularity of the order of a sub-micrometer on the side walls for raising the strength of adhesion. This irregularity improves an adhesiveness of the conductive film connected to the SiN, which is the same material as an invested membrane, and the upper electrode. It also improves an adhesiveness of a later described ultrasonic attenuation material, leading to an improvement of strength when dicing by a precision dicing.

As such, the forming of surface irregularity on the side surface of the trench by using the Bosh process enlarges a surface area size and makes an electrode film and SiN film which are invested by the process thereafter hard to come off. Meanwhile, the GND of the contact electrodes 72 (i.e., 72a, 72b and 72c) existing on the bottom of the trench is connected to a contact electrode 74 by way of the silicon substrate 76.

The trench on the left side of FIG. 8 exemplifies the case of the bottom being wider than the opening part. As such, the feature of the trench may be discretionary.

Figure 9:
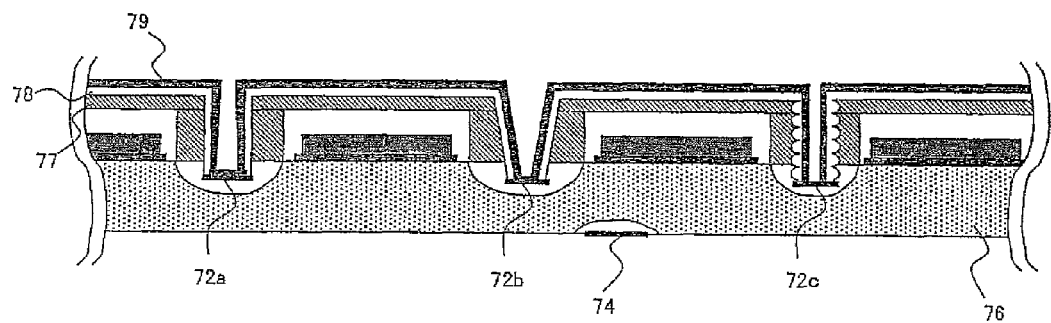
FIG. 9 is a diagram exemplifying a variation of a trench form according to the first-2 embodiment (part 2)

FIG. 9 exemplifies a variation of a trench form according to the present embodiment (part 2). FIG. 9 shows the case of cutting the bottom of the trench deeper into the inside of a silicon substrate 76 than the case of FIG. 8. This is produced by etching down to the silicon substrate 76, followed by forming a contact layer 73 and filming an electrode with the contact layer 73 as the base. That is, the forming of the contact layer is followed by forming an SiN film (i.e., closing the hole for removing a sacrifice layer) by means of the CVD and filming a strong corrosion-resistant electrode member as a base electrode before filming an electrode 79 which is connected to a membrane so that the contact layer surface does not have a resistance due to such as natural oxidization.

As described above, the distance between the contact electrodes 72 (i.e., 72a, 72b and 72c) and contact electrode 74 becomes shorter, reducing an electrical loss, thereby improving a reliability of the wiring.

Since a dry etching is employed, it is possible to apply etching in wavy line provided that there is no problem of a mechanical strength. That is, a common trench forming (likewise a shearing) is carried out by using a dicing saw, which is only capable of forming a straight line trench. However, a dry etching such as ICP-RIE is capable of forming a trench of discretionary form, such as a wavy form.

Meanwhile, if a trench surface is an indeterminate form, a determinate resonance is difficult to occur because lengths are different and therefore it is beneficial in reducing a crosstalk. Also beneficial is that it is easy to take out a ground electrode to the back of the substrate.

The configuration of having a trench in the silicon substrate provides a benefit of reducing a crosstalk. That is, an ultrasound is transmitted and received by a flexion movement of the membrane, and the flexion movement allows a generation of crosstalk between the adjacent elements due to an vibration such as Lamb wave and Stoneley wave. The flexion movement transmits a reactionary longitudinal vibrating stress to the member supporting membrane. This vibration reaches at a silicon substrate surface from base parts of the member supporting membrane, propagates along the surface of the silicon substrate, and propagates reversely along the same path to the next neighbor element, thus causing a crosstalk. It is possible to reduce an occurrence of such a crosstalk.

Figure 10:
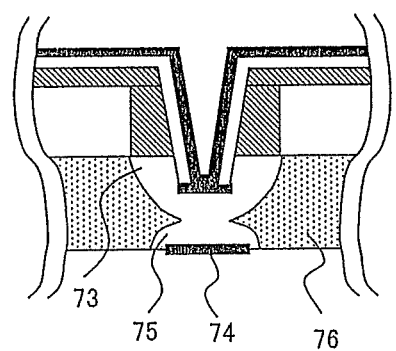
FIG. 10 is a diagram exemplifying a variation of a trench form according to the first-2 embodiment (part 3)

FIG. 10 exemplifies a variation of a trench form according to the present embodiment (part 3). FIG. 10 shows the case of joining contact layers on both faces of a silicon substrate 76. In the case of the silicon substrate being thin as shown in FIG. 10, or of etching a (GND-use) trench on the silicon substrate, followed by forming contact layers 73 and 75, diffusing them, and forming the contact layers, then the thin contact layers can be mutually connected. This configuration forms a low resistance zone between a contact electrode 72 and contact electrode 74, making an easy electrical conduction and reducing an electrical loss, thereby improving a reliability of a wiring.

First-3 Embodiment

Described for the present embodiment is a variation of a c-MUT element.

Figure 11:
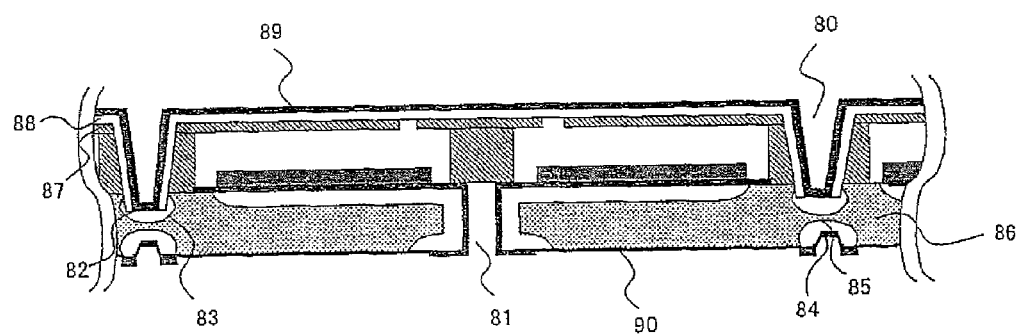
FIG. 11 is a diagram exemplifying a variation of a c-MUT element according to the first-3 embodiment (part 1)

FIG. 11 is a diagram exemplifying a variation of a c-MUT element according to the present embodiment (part 1).

The numerical 80 indicates a trench. The 86 indicates a silicon substrate. The 82 indicates a contact electrode on the upper face side of the silicon substrate 86. The 83 indicates a contact layer formed in the neighborhood of the contact electrode 82. The 84 indicates a contact electrode on the bottom face side of the silicon substrate. The 85 indicates a contact layer formed in the neighborhood of the contact electrode 84. The 87 and 88 indicate SiN layers, respectively. The 89 indicates an electrode film. The 90 indicates an $SiO_2$ film. The 81 indicates a through-hole electrode from bottom electrode.

FIG. 11 shows the case of the etching also applied to the surrounding area of the contact electrode on the bottom face of the silicon substrate 86. This configuration is for masking also the bottom surface of the silicon substrate with $SiO_2$ at the stage of the step 1 shown in FIG. 7 and applying the etching to the electrode contact part by means of a wet etching so as to make it concave form. This configuration further shortens the distance between the contact electrodes (82 and 84) on both faces and accordingly reduces an electrical loss and therefore the reliability of wiring is improved.

Also, the adoption of the configuration of the trench invading the silicon substrate 86 provides a benefit of reducing a crosstalk as in the case of FIG. 9. That is, while it transmits and receives an ultrasound by the flexion movement of the membrane, the flexion movement generates a crosstalk between the adjacent elements due to a Lamb wave or Stoneley wave. The flexion movement transmits a reactionary longitudinal vibrating stress to the member supporting membrane. This vibration reaches at a silicon substrate surface from base parts of the member supporting membrane, propagates along the surface of the silicon substrate, and propagates reversely along the same path to the next neighbor element, thus causing a crosstalk. It is possible to reduce an occurrence of such a crosstalk by adopting the configuration of the trench invading the silicon substrate 86. It also provides the benefit of easing an extraction of the ground electrode to the back of the substrate.

Note that a Wet oxidization film of $SiO_2$ may be utilized instead of forming the depletion layer. The reason is that the Wet oxidization film can obtain more exact film. Also, it may be possible to apply an N+ doping in the trench if it is an N type silicon substrate after forming the trench and apply a diffusion process by heating, thereby forming a contact layer (N+). Meanwhile, the trench may be such that a part of the bottom is deeper, or that a hole reaches at the bottom face of the silicon substrate.

Figure 12:
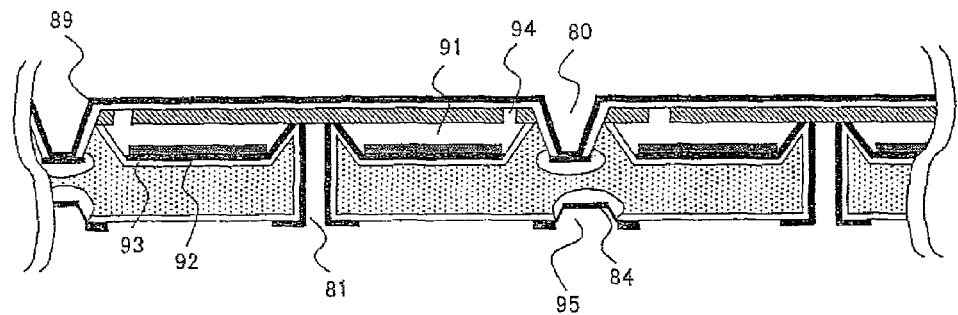
FIG. 12 is a diagram exemplifying a variation of a c-MUT element according to the first-3 embodiment (part 2)

FIG. 12 exemplifies a variation of a c-MUT element according to the present embodiment (part 2). FIG. 2 shows the case of forming a cavity 91 by applying an etching to a silicon substrate 86. In this case, the silicon substrate 86 also functions as member supporting membrane.

First process applies an anisotropic etching to Si by using Tetramethyl Ammonium Hydroxide (TMAH). This process forms a cavity 91 and a trench 80 of a prescribed depth on the upper face side of the silicon substrate 86 and a concave part 95 on the bottom face side thereof.

The next forms a through hole 81 by means of the ICP-RIE. It is followed by filming applying a Wet oxidization for forming an oxide film 90 (used as a substitute for a depletion layer). Then forms a film of the bottom electrode 92 (Pt/Ti) to invest the side wall of the through hole 81 with a conductor.

The next forms a film of a dielectrics 93 on the top surface of the bottom electrode 92, followed by applying a heat treatment. Then forms a sacrifice layer in the cavity 91 and films an SiN membrane 87 over the sacrifice layer. Then putting a hole 94 in the filmed membrane and remove the sacrifice layer by applying an etching. It is followed by closing the hole used for a removal of the sacrifice layer by SiN. It is then covered over with an upper electrode 89.

This process eliminates a necessity of adding a specific process for forming the member supporting membrane, thereby enabling a reduction of the number of processes.

Figure 13:
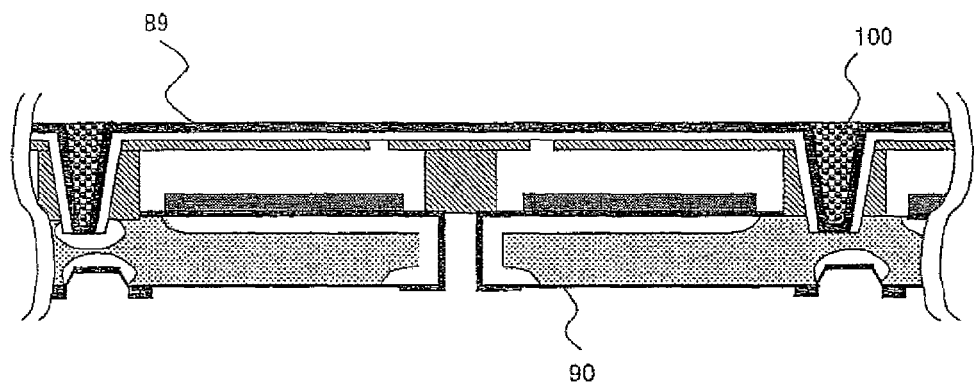
FIG. 13 is a diagram exemplifying a variation of a c-MUT element according to the first-3 embodiment (part 3)
Figure 14:
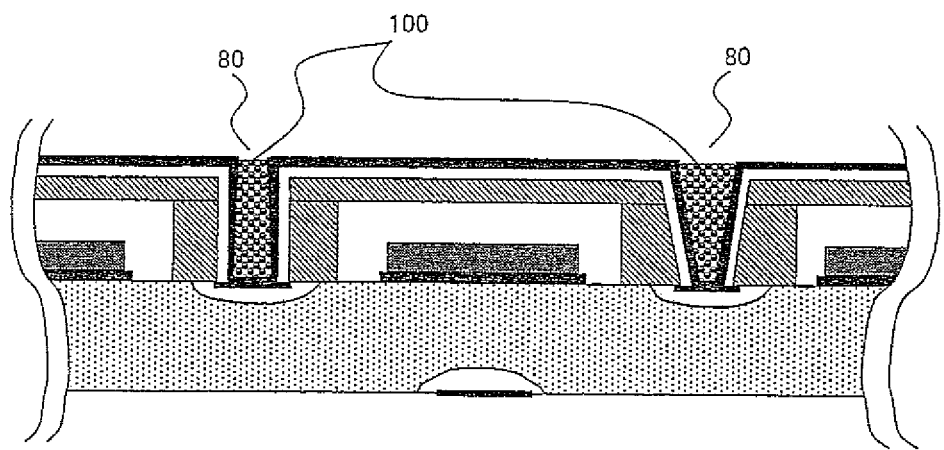
FIG. 14 is a diagram exemplifying a variation of a c-MUT element according to the first-3 embodiment (part 4)

FIG. 13 exemplifies a variation of a c-MUT element according to the present embodiment (part 3). FIG. 14 exemplifies a variation of a c-MUT element according to the present embodiment (part 4). FIGS. 13 and 14 show the case of filling a trench 80 with a resin 100.

The difference between FIGS. 13 and 14 is either a contact electrode on the bottom face of a silicon substrate 86 is formed in a concave or not. If the trench 80 is not filled with the resin 100, a transverse standing wave (i.e., an extraneous vibration) may be excited within a transducer, thus unable to obtain a good ultrasonic characteristic. Therefore, the trench 80 is filled with the resin 100. Its material uses, as an ultrasonic attenuation material, a flexible composite resins mixing such material as a silicone resin, epoxy resin and urethane resin with powder of such material as tungsten fine powder and glass bubble in order to attenuate an vibration caused by an extraneous ultrasound. This configuration makes it possible to suppress an extraneous vibration.

Incidentally, among the trenches shown in FIGS. 3 through 6 (i.e., the trenches are featured vertically and horizontally when viewing the transducer elements from above), the types of transducers having a curved array of the transducers as in the case of the convex and radial types are applied by a dicing on at least one side (e.g., the top face side). If a filled resin exists in such an event, a stress is reduced so as to decrease a peeling, chipping or such of an electrode. Such decrease of a chipping as well as an improvement of a reliability of a wiring can shorten the distance between the cavity and trench, resulting in increasing a working part from a design view point, thereby leading to an increased sound pressure per unit area size, that is, an improved sensitivity and a miniaturization of size.

Figure 15:
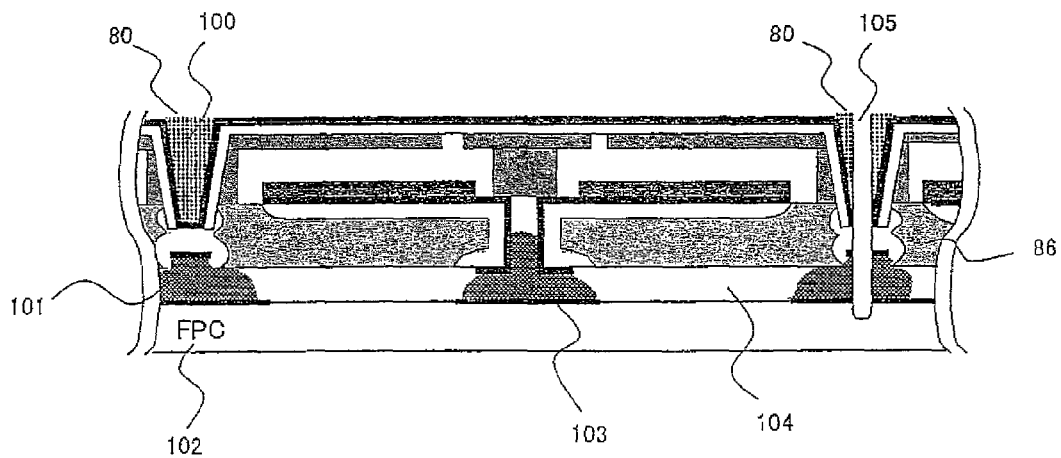
FIG. 15 is a diagram exemplifying a variation of a c-MUT element according to the first-3 embodiment (part 5)

FIG. 15 exemplifies a variation of a c-MUT element according to the present embodiment (part 5). FIG. 15 is a diagram showing the case of joining a transducer element to a flexible printed circuit (FPC) by using a conductive resin 101. Note that an anisotropic conductive film (ACF) or a ball bump made of such material as Au and solder in place of the conductive resin 101. Also, an air gap 104 between the FPC and the lower face of the silicon substrate 86 may be filled with a resin.

Also, the trench 80 may be featured with a dicing trench 105 by dicing in place of filling with a resin, or the trench 80 may be filled with a resin followed by featuring a dicing trench 105 by dicing. Or, it may be such that a forming of a transducer by curving after a dicing, followed by filling with a resin material having a large attenuation. As for a depth of the dicing trench, the dicing must be as deep as reaching the conductive resin 101 if it is a type curving the transducer elements such as a convex type and radial type; while a type not curving the elements, such as a linear type, however, al least the silicone substrate needs to be diced. Meanwhile, if an electrode 103 of a silicon on the FPC side is formed as concave or hole, a positioning function is obtained and also a mechanical strength of the connection due to an expansion of an adhering area size, thereby enabling a production of a highly reliable transducer.

Also, a laser beam may be used for penetrating a silicon substrate. The use of the laser beam enables a trench cutting or shearing of a discretionary form, likewise a dry etching. This obtains a benefit of reducing a crosstalk, and making a wavy line increases a contact area size increases, increasing adhesion strength. Also, an ability of making a form of elements discretionary enables a discretionary cell layout, thereby making it possible to achieve a high density configuration (e.g., an area size ratio of cells to that of an element is large), which is very important for accomplishing a high sensitivity within a limited space such as endoscope.

Figure 16A:
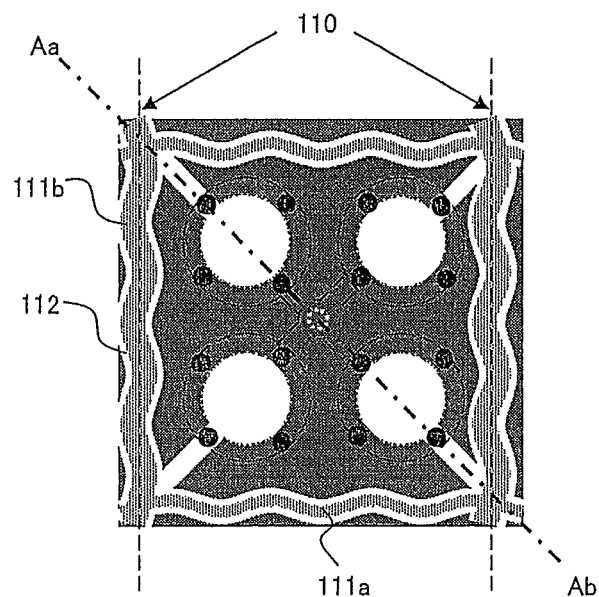
FIG. 16A is a diagram exemplifying the case of forming a trench of a curved line when viewing the transducer element according to the first-3 embodiment from above.
Figure 16B:
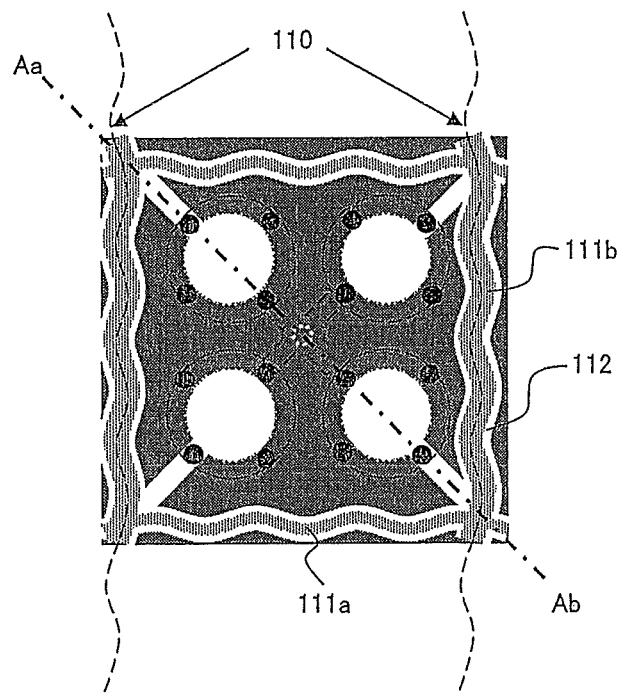
FIG. 16B is a diagram exemplifying the case of forming a trench of a curved line when viewing the transducer element according to the first-3 embodiment from above.
Figure 16C:
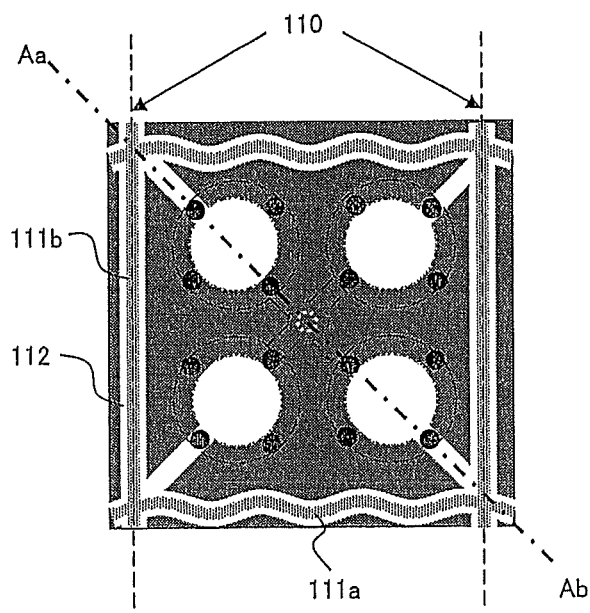
FIG. 16C is a diagram exemplifying the case of forming a trench of a curved line when viewing the transducer element according to the first-3 embodiment from above.

Incidentally, a trench is commonly straight as shown in FIG. 5 when viewing a transducer element from above, it is, however, possible to form a curved trench if a photolithography and an etching are applied. FIGS. 16A, 16B and 16C exemplify it.

FIG. 16 (i.e., FIGS. 16A, 16B and 16C) is a diagram exemplifying the case of forming a trench of a curved line when viewing the transducer element 3 according to the present embodiment from above. FIG. 16A exemplifies the case of making trenches 111 (i.e., a horizontal trench 111*a* and a vertical trench 111*b*) surrounding a transducer element 3 curved lines and dicing in straight lines (i.e., dicing lines 110). As such, all around the transducer element may have a wavy line trench.

FIG. 16B exemplifies the case of making trenches 111*a* and 111*b* surrounding a transducer element curved line and dicing in curved lines (i.e., dicing lines 110). It is possible to apply a dicing along the curved trench by employing a laser dicing.

FIG. 16C exemplifies the case of making a vertical direction trench 111*b* a straight line and a horizontal direction trench a curved line, among the trenches surrounding a transducer element, and dicing in straight lines (i.e., dicing lines 110). The numerical 112 is a ground electrode. As such, it may have a partly wavy line trench structure.

In addition to the examples shown in FIG. 16, a trench form and a dicing form may apparently be a rectangular wave form, saw-tooth wave form, or indeterminate form.

A resonance is stronger and accordingly a standing wave tends to occur in the case of a straight line trench, while extraneous vibrations are weaker as a result of canceling each other in the case of a non-straight line trench. This accordingly reduces a crosstalk, improves an S/N ratio and provides a high image quality image. Note that an adoption of the same dicing position and ultrasonic attenuation resin as that of a straight line configuration makes it possible to obtain the same function and effect.

As described above, the first embodiment is configured to eliminate a necessity of decreasing an area size ratio of a cell zone to the entirety of a c-MUT featured with trenches respectively on both ends of a transducer element, thereby negating a possibility of reducing an output of a generated ultrasound.

Second Embodiment

A description for the present embodiment is on an endo cavity ultrasonic diagnosis system enabling a noncontact diagnosis by using a radial scanning type c-MUT, in addition to being capable of obtaining a tomographic image by being stationary in contact with an endo cavity wall similar to a conventional technique.

Figure 17:
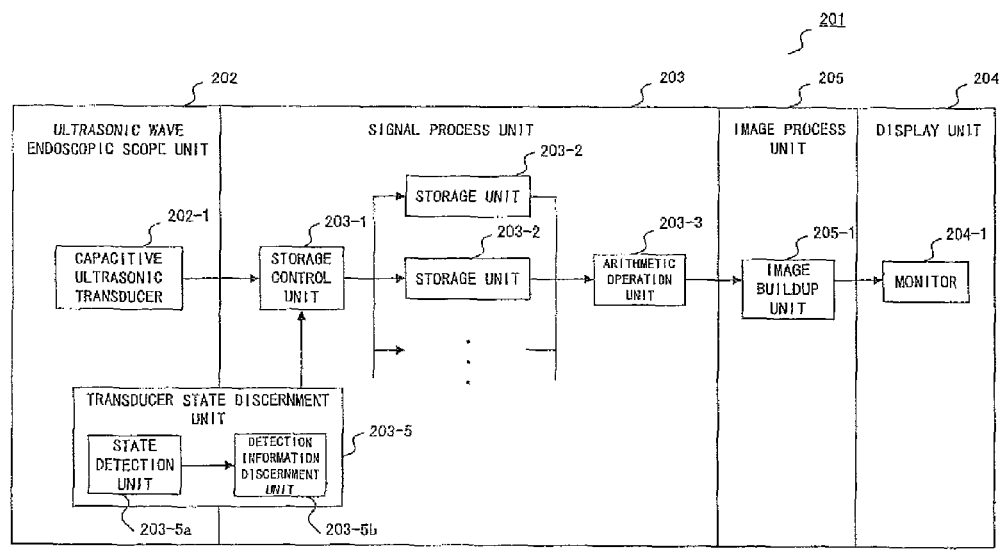
FIG. 17 is a diagram showing an outline of an endo cavity ultrasonic diagnosis system according to a second embodiment.

FIG. 17 shows an outline of an endo cavity ultrasonic diagnosis system according to the present embodiment. Referring to FIG. 17, the endo cavity ultrasonic diagnosis system 201 primarily comprises an ultrasonic endoscopic scope unit 202, a signal process unit 203, an image process unit 205 and a display unit 204. Note that FIG. 17 indicates only a reception signal series, while omitting a transmission signal series from the drawing.

The ultrasonic endoscopic scope unit 202 is equipped with a c-MUT 202-1 on the head part thereof. The primary functions of the c-MUT 202-1 is for first inserting the head part of the ultrasonic endoscopic scope unit 202 into an endo cavity, transmitting an ultrasound from the c-MUT 202-1, receiving an ultrasound reflected within the endo cavity thereby and converting the received ultrasound into an electric signal.

The signal process unit 203 analyzes the electric signal obtained by the ultrasonic endoscopic scope unit 202 and performs an arithmetic operation of it. The signal process unit 203 comprises a storage control unit 203-1, a storage unit 203-2, an arithmetic operation unit 203-3 and a transducer state discernment unit 203-5.

The transducer state discernment unit 203-5 is configured for discerning a state of the c-MUT, for example, whether the c-MUT 202-1 is on the outside of a human body or in the inside thereof and not in contact with an endo cavity wall, or in contact therewith. The transducer state discernment unit 203-5 is constituted by a state detection unit 203-5*a* and a detection information discernment unit 203-5*b*. The state detection unit 203-5*a* is for detecting a state of the c-MUT 202-1. The detection information discernment unit 203-5*b* is for discerning a state of the c-MUT 202-1 based on information detected by the state detection unit 203-5*a*. Note that the transducer state discernment unit 203-5 may be included in the ultrasonic endoscopic scope unit 202, in the signal process unit 203, or in both of them in accordance with the discernment method.

The storage unit 203-2 is for storing sense information (e.g., received reflection wave and standing wave) sensed by the c-MUT 202-1. A plurality of storage units 203-2 exists. Note that a plurality of physical storage units or logical zones may exist (i.e., securing a plurality of logical storage zones within a single storage apparatus, with each storage zone being handled as a storage unit).

The storage control unit 203-1 is for storing sense information sensed by the c-MUT 202-1 in a storage unit 203-2 corresponding to a discernment result based on the discernment result of the transducer state discernment unit 203-5.

The arithmetic operation unit 203-3 is for performing an arithmetic operation (e.g., a difference and a correlation function) based on the sense information stored in each storage control unit 203-2. A plurality of combinations of arithmetic operations exists, enabling the operation in accordance with each purpose.

The image process unit 205 is constituted by an image buildup unit 205-1. The image buildup unit 205-1 is for building up an ultrasonic diagnosis image (e.g., a contour image of an endo cavity wall, an endo cavity organization section image, or an image that combines the aforementioned) from the operated signal based on the result of the arithmetic operation at the arithmetic operation unit 203-3.

The display unit 204 is for displaying an ultrasonic diagnosis image generated at the image process unit 205, including a monitor (i.e., a display) 204-1 for example. Note that the display unit 204 may be output equipment such as a printer, in lieu of being limited to a display.

Figure 18:
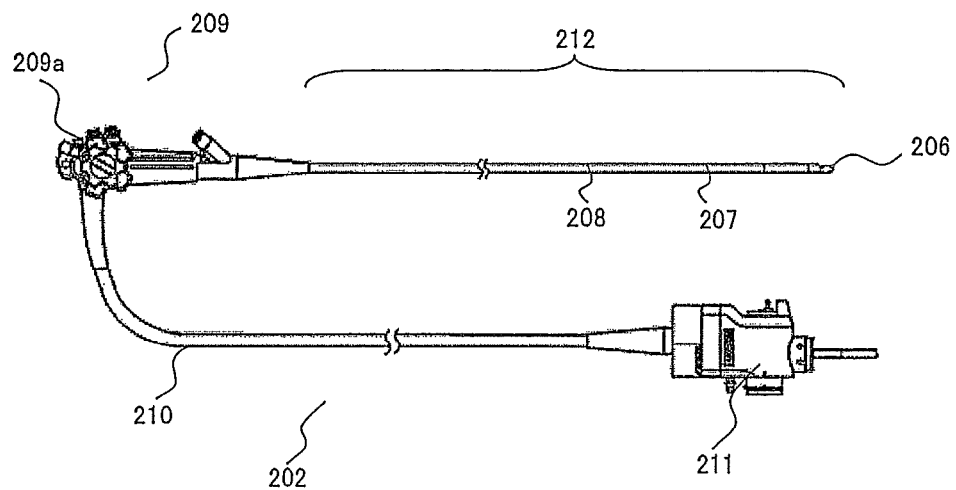
FIG. 18 is a diagram showing an external configuration of an ultrasonic endoscopic scope according to the present embodiment of the second embodiment.

FIG. 18 shows an external configuration of the ultrasonic endoscopic scope 202 according to the present embodiment. The ultrasonic endoscopic scope 202 comprises a control section 209 on the base end of a slender insertion tube 212, and a scope connector 211 on one end. From a side part of the control section 209 extends a universal cord 210 to be connected to a light source apparatus (not shown herein). The scope connector 211 is further connected to the signal process unit 203.

The insertion tube 212 is constituted by serially connecting, from the head side, a capacitive radial sector scanning array ultrasonic transducer 206 equipped on the head part, a freely bending section 207, and a flexible tube section 208 having flexibility. The control section 209 is equipped with a bending control knob 209a, enabling a curving of the bending section 207 by operating the bending section knob 209a. The head part is also equipped with an illumination lens cover, constituting an illumination optical part for transmitting an illumination light onto an observation region, an observation-use lens cover constituting an observation optical part for capturing an optical image of an observation region, a forceps exit that is an opening for projecting a treatment instrument, and such, which are not shown herein.

Figure 19:
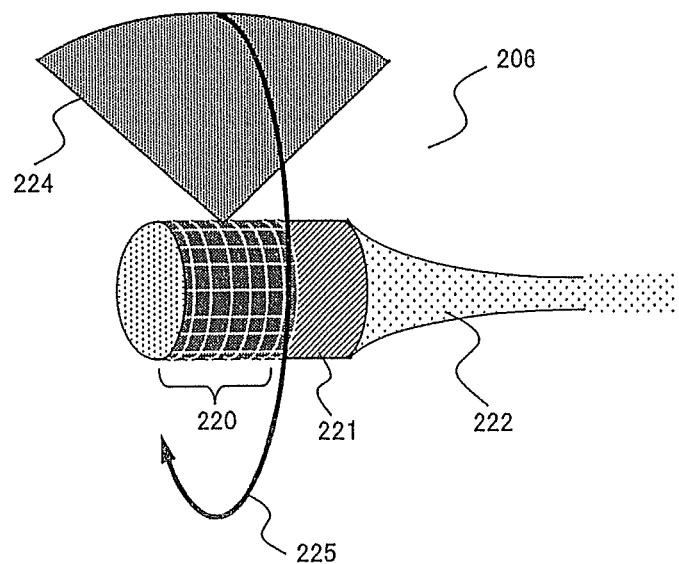
FIG. 19 is a diagram showing a comprisal of a capacitive radial and sector scanning array ultrasonic transducer according to the second embodiment.

FIG. 19 is a diagram showing a comprisal of a capacitive radial sector scanning array ultrasonic transducer 206 (named as "ultrasonic transducer", or "transducer" hereinafter) equipped on the head part of the ultrasonic endoscopic scope unit 202 shown in FIG. 18. The ultrasonic transducer 206 is constituted by a two-dimension array transducer 220, a transmission/reception circuit 221 and a coaxial cable bundle 222. The two-dimension array transducer 220 is formed by arraying a plurality of transducer elements. The coaxial cable bundle 222, being housed in the insertion tube 212, is made by bundling a plurality of cables connected to the individual transducer elements. The transmission/reception circuit 221 is for controlling signals exchanged with the transducer elements. That is, the transmission/reception circuit 221 is capable of controlling a scanning of a compound ultrasonic beam transmitted from the ultrasonic transducer 206, and capable of performing not only a radial scan 225 but also a sector scan 224 (i.e., an ultrasound sector scanning plane) within a single element (in the cylindrical longitudinal direction). This configuration enables a buildup of a three-dimensional ultrasonic image. The two-dimensional array transducer has been described in detail for FIGS. 3 through 6 of the first embodiment, and therefore it is omitted here.

The next description is on a series of flow of operation of the endo cavity ultrasonic diagnosis system 201 according to the present embodiment.

Figure 20:
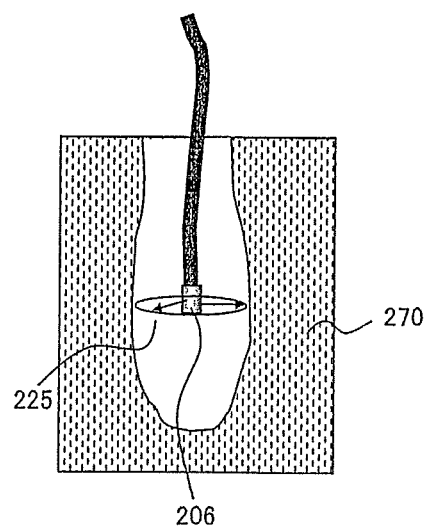
FIG. 20 is a diagram showing an ultrasonic anechoic cell according to the second embodiment.

FIG. 20 shows an ultrasonic anechoic cell 270 according to the present embodiment. A cavity is featured in the inside of the ultrasonic anechoic cell 270, and the ultrasonic transducer 206 is inserted from the opening thereof as shown in FIG. 20, followed by transmitting an ultrasound. In this event, the ultrasound is not reflected because the ultrasonic anechoic cell 270 is structured by a member absorbing the ultrasound (e.g., a urethane fiber, a foamed silicone resin or the like). Therefore, transmitting an ultrasound by an ultrasonic transducer within the ultrasonic anechoic cell 270, a reflectance wave is not received. Therefore, a charge of the upper electrode does not change at the time of reception because the membrane basically does not vibrate. In the case of an extraneous vibration such as a standing wave occurring, however, the charge on the membrane is changed by the influence, thus requiring a detection of a change in the charge in this case. That is, an extraneous vibration which is not converted into a transmission ultrasound remains as a standing wave associated with an vibration of the membrane at the time of transmission, and the vibration is overlapped as a noise signal at the time of an actual echo reception, ushering in decreasing an S/N ratio.

Figure 21B:
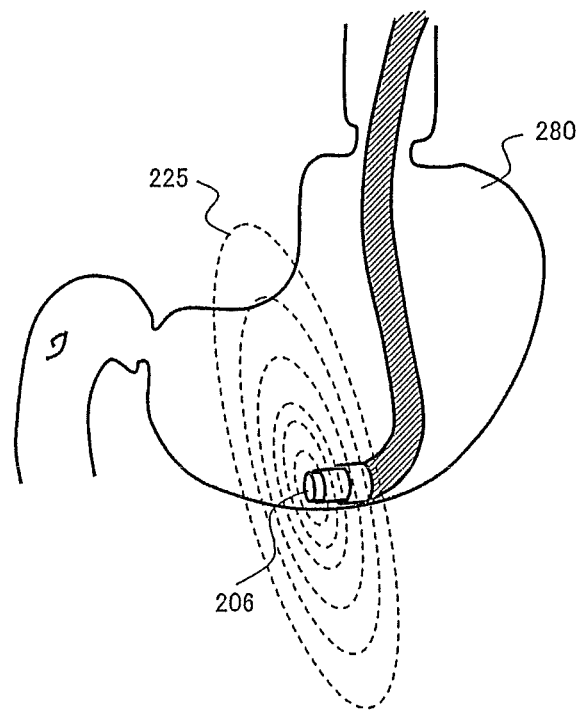
FIG. 21B is a diagram showing the case of inserting, into an endo cavity (i.e., in the states of contacting an ultrasonic transducer with the inside wall of a stomach and transmitting/receiving an ultrasound), an ultrasonic transducer according to the second embodiment.

FIG. 21 (FIGS. 21A and 21B) show a state of inserting the ultrasonic transducer 206 into an endo cavity, with FIG. 21A showing a state of inserting it into a mouth and FIG. 21B showing a state of transmitting and receiving an ultrasound by having the ultrasonic transducer 206 contact with a stomach wall.

The transmission and reception of an ultrasound is performed in three states, i.e., the case of performing it in an ultrasonic anechoic cell 270 (refer to FIG. 20) (named as "state 1" hereinafter), the case of performing it in the air (not in contact with an endo cavity wall) between the insertion into an endo cavity and arrival at an observation region (refer to FIG. 21A) (named as "state 2" hereinafter) and the case of performing it with the ultrasonic transducer in contact with an endo cavity wall (refer to FIG. 21B) (named as "state 3" hereinafter).

In the case of using a conventional piezoelectric element, it has been only possible to obtain an ultrasonic image in the state of the element in contact with an observation region, whereas a c-MUT, having an acoustic impedance of the ultrasonic transmission/reception face larger than the air and smaller than a live tissue, thus making it possible to obtain an ultrasonic image in the air (i.e., a state of not in contact with an endo cavity wall). This makes it possible to easily obtain a reflectance wave from an endo cavity wall, enabling a measurement of a contour of a luminal wall, that is, a surface irregularity, while inserting the ultrasonic transducer. The c-MUT is capable of transmitting and receiving a high frequency ultrasound of ones MHz, thus enabling a high accuracy detection of a surface irregularity.

Figure 22:
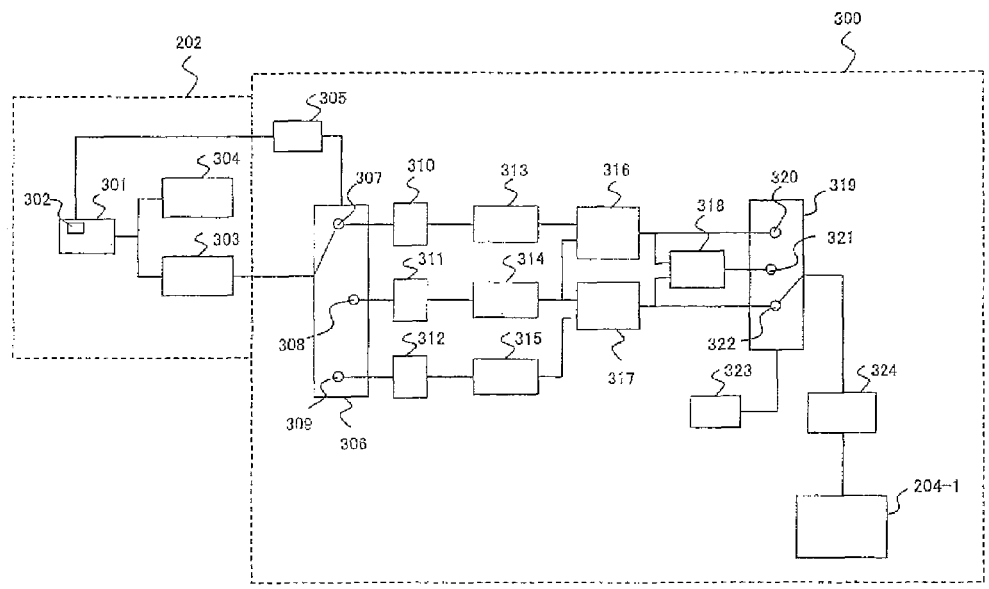
FIG. 22 is a diagram showing an outline of an internal comprisal of an endo cavity ultrasonic diagnosis system according to the second embodiment.

FIG. 22 shows an outline of an internal comprisal of an endo cavity ultrasonic diagnosis system according to the present embodiment. The endo cavity ultrasonic diagnosis system is constituted by an ultrasonic endoscopic scope unit 202 and an ultrasonic endoscope diagnostic apparatus 300.

The ultrasonic endoscopic scope unit 202 comprises a c-MUT 301, an optical sensor 302, a charge amplifier 303 and a pulser (i.e., a pulse generation circuit) 304.

The ultrasonic endoscope diagnostic apparatus 300 comprises an signal process circuit for optical sensor 305, a switch circuit 306 (including a selection SW1 for terminals (307), a selection terminal SW2 (308), and a selection terminal SW3 (309)), AD converters 310, 311 and 312, storage apparatuses 313, 314 and 315, arithmetic operation circuits 316, 317 and 318, a switch circuit 319 (including a selection terminal Q1 (320), a selection terminal Q2 (321) and a selection terminal (322)), an operation unit 323, an image converter (i.e., a digital scan converter) 324, and a monitor 204-1.

The pulser 304 is a circuit for generating an electric signal for driving the c-MUT 301.

The charge amplifier 303 comprises the function of performing an impedance conversion (i.e., converting from a high impedance to a low impedance), that of detecting a charge on an electrode surface of the c-MUT 301 and that as amplifier. The function of detecting a charge is to detect a charge as a result of the c-MUT 301 receiving a reflectance wave, causing the membrane to vibrate in accordance with the reception intensity of the reflectance wave and causing a variation of the charge on the upper electrode in response to the vibration. Note that the present embodiment is configured by assuming the case of detecting not only the charge caused by receiving a reflectance wave but also a charge caused by an extraneous vibration such as a standing wave. These are included in a term "reception signal" in the following description.

The optical sensor 302 is for detecting a brightness of the surrounding area of the c-MUT 301.

The signal process circuit for optical sensor 305 is for discerning a brightness/darkness based on a signal output from the optical sensor 302. That is, it is capable of analyzing a signal based on the light volume detected by the optical sensor and discerning a difference of brightness in the surrounding of the c-MUT 301.

An example configuration is so as to detect the highest brightness among the above described three states in the case of transmitting and receiving before inserting the ultrasonic transducer 301 into an endo cavity, that is, in the ultrasonic anechoic cell 270 (i.e., the state 1). Then, a brightness is decreased when inserting the ultrasonic transducer 301 into an endo cavity until reaching at an observation region (i.e., the state 2), and therefore the configuration is for detecting the reduced brightness. Then, when the ultrasonic transducer reaches at an observation region (i.e., the state 3), it is configured to detect reflectance light as a result of the light emitted from the light guide (not shown herein) equipped in the surrounding of the ultrasonic transducer being reflected by the endo cavity wall, and therefore it is capable of detecting a higher brightness than the state 2.

Therefore, the setup of discernment information for the signal process circuit for optical sensor 305 is such that the ultrasonic transducer 301 is judged to be prior to an insertion into an endo cavity (i.e., the state 1) at an initial state. Then, the brightness decreases from the insertion into an endo cavity until reaching at an observation region (i.e., the state 2), and therefore the judgment is a state of the state 2 if a signal from the optical sensor indicates a value equal to or lower than a threshold value. Then, if the brightness increases and if a signal from the optical sensor indicates a value equal to or higher than the threshold value, the ultrasonic transducer is judged to be in contact with an observation region (i.e., the state 3).

The switch circuit 306 is for turning on and off the selection terminals SW1, SW2 and SW3 in response to an output of the signal process circuit for optical sensor 305. If the signal process circuit for optical sensor 305 judges that the ultrasonic transducer is in a state of being prior to an insertion into an endo cavity (i.e., the state 1), it outputs a signal effecting the state so that the selection SW1 for terminals (307) is turned On as a result of receiving the signal at the switch circuit 306. If the signal process circuit for optical sensor 305 judges that the ultrasonic transducer is in a state of being inserted into an endo cavity and on the move to an observation region (i.e., the state 2), it outputs a signal effecting the state so that the selection terminal SW2 (308) is turned On as a result of receiving the signal at the switch circuit 306. And, if the signal process circuit for optical sensor 305 judges that the ultrasonic transducer is in a state of reaching at an observation region (i.e., the state 3), it outputs a signal effecting the state so that the selection terminal SW3 (309) is turned On as a result of receiving the signal at the switch circuit 306.

A reception signal based on charge information detected at the charge amplifier 303 is input to either of the AD converter 310, 311 or 312 based on the destination of a changeover of the switch circuit 306. The AD converter 310, 311 or 312 converts the input analog signal into a digital signal. The converted signal is input to either of the storage apparatus 313, 314 or 315, to be stored therein, corresponding to the AD converter 310, 311 or 312.

The arithmetic operation circuits 316, 317 and 318 calculate a correlation function among the reception signals (i.e., respective signals stored in the storage apparatuses 313, 314 and 315) obtained in the individual states, thereby making it possible to remove, from the respective reception signals of the states 2 and 3, an extraneous vibrational wave component such as a standing wave that is a noise component obtained in the state 1.

The correlation function includes a cross-correlation function and an autocorrelation function. Explaining the case of using a cross-correlation function, it is the function of a shift amount of τ when a waveform of one of two signals is delayed for the τ and is defined as the following expression:

$$R_{xy}(t) = \lim_{T\to 0} \frac{1}{T} \int_{-T/2}^{T/2} x(t)y(t+\tau)\,dt; \quad (1)$$

where x(t) is a waveform based on a reception signal in the state of "m" (where an m is discretionary), and y(t) is a waveform based on a reception signal in the state of "n" (where an n is discretionary).

The use of the cross-correlation function $R_{xy}$ enables a calculation of similarity between two signals. If the two signals are completely different from each other, the cross-correlation function $R_{xy}$ is close to zero regardless of a τ. This accordingly makes it possible to detect a component of an extraneous vibration such as a standing wave and accordingly remove the component. Note that a cross-correlation function $R_{xy}$ can be obtained by applying an inverse Fourier transform to a cross-spectrum.

Meanwhile, an autocorrelation function can also be used. The autocorrelation function is a function of a shift amount of τ using a waveform x(t) and a waveform x(t+τ) that is displaced by τ and it is defined by the following expression:

$$R_{xx}(t) = \lim_{T\to 0} \frac{1}{T} \int_{-T/2}^{T/2} x(t)x(t+\tau)\,dt \quad (2)$$

The autocorrelation function $R_{xx}$ becomes a maximum with τ=0, that is, when it is substituted by a product of itself so that, if a waveform is cyclic, the autocorrelation function indicates peaks in the same cycle as the waveform. If it is an irregular signal and a variation occurs slowly, the autocorrelation function indicates a high value where a τ is large, or if the variation occurs quickly, then the autocorrelation function indicates a high value where a τ is small, thus making the τ a temporal indication of a variation. This makes it possible to detect a component of an extraneous vibration such as a standing wave, and accordingly remove the component. Note that an autocorrelation function can be obtained by applying an inverse Fourier transform to a power spectrum.

Note also that another configuration may be so as to remove an extraneous component such as a standing wave by calculating a difference between a waveform based on a reception signal in a state of "m" and that based of a reception signal in a state of "n", other than the method of using a correlation function.

Input to the arithmetic operation circuit 316 are a signal stored in the storage apparatus 313 (i.e., the reception signal in the state 1) and a signal stored in the storage apparatus 314 (i.e., the reception signal in the state 2). The arithmetic operation circuit 316 calculates a correlation of the two signals or a difference between the two, thereby removing a component of an extraneous vibration from the reception signal in the state 2.

Input to the arithmetic operation circuit 317 are a signal stored in the storage apparatus 314 (i.e., the reception signal in the state 2) and a signal stored in the storage apparatus 315 (i.e., the reception signal in the state 3). The arithmetic operation circuit 317 likewise calculates a correlation of the two signals or a difference between the two, thereby removing the reception signal in the state 2 from that in the state 3. This configuration makes it possible to remove also an extraneous vibration component simultaneously.

The arithmetic operation circuit 318 calculates a sum of the signals obtained by the arithmetic operation circuits 316 and 317. This obtains a contour image (i.e., surface irregularity information of a luminal wall) and a cross-section image (i.e., information of a depth direction) thereof simultaneously. Note that a correlation of signals obtained at the arithmetic operation circuits 316 and 317 may be calculated by using a correlation function.

The operation unit 323 is for performing a changeover operation of the switch circuit 319. An operation of the operation unit 323 changes over the switches included in the switch circuit 319, thereby enabling a selection of an image in a state of a desired output. That is, a signal subjected to an arithmetic operation at the arithmetic operation circuit 316 can be output to the image converter 324 if the selection terminal Q1 (320) is selected. A signal subjected to an arithmetic operation at the arithmetic operation circuit 318 can be output to the image converter 324 if the selection terminal Q2 (321) is selected. And a signal subjected to an arithmetic operation at the arithmetic operation circuit 317 can be output to the image converter 324 if the selection terminal Q3 (322) is selected.

A signal prior to being input to the image converter 324 is a time axis signal; it is, however, converted into an image signal by way of the image converter 324. And thus obtained image signal is output to the monitor 204-1 and an ultrasonic diagnosis image is displayed therein.

As described above, the use of the c-MUT makes it possible to transmit and receive an ultrasound both in the states of the ultrasonic transducer in contact with, and not in contact with, an endo cavity wall, and transmit reception signals of the ultrasound received in the respective states to the respectively corresponding channels.

A "noncontact diagnosis" is enabled in addition to the capability of obtaining a cross-sectional image by fixing the ultrasonic transducer in contact with an endo cavity wall. The "noncontact diagnosis" makes it possible to obtain organization feature information of a luminal wall in the process of inserting the ultrasonic transducer into the endo cavity. That is, an ultrasonic diagnosis which used to be impossible to perform by the conventional ultrasonic diagnosis.

Also, performing a signal process for calculating a correlation or difference between reception signals obtained by the respective states makes it possible to remove a standing wave component (i.e., a noise component) that is an extraneous vibration, thereby enabling an obtainment of a clearer ultrasonic diagnosis image than before.

Also, an extraneous vibration component such as a standing wave that is a noise component can be removed from an ultrasonic diagnosis image, thereby enabling an obtainment of a clearer image signal. By this, it is possible to obtain an ultrasonic diagnosis image that expresses a clear contour feature of an endo cavity wall even if the ultrasonic diagnosis image is photographed in a state of the ultrasonic transducer not in contact with the endo cavity wall.

Also, performing a signal process by combining reception signals obtained in respective states is capable of obtaining a contour image, and an endo cavity cross-section image, of an endo cavity wall.

Also, a use of detection means such as an optical sensor enables a detection of whether or not the ultrasonic transducer contacts with an endo cavity wall and therefore a state of the ultrasonic transducer can be detected.

Note that the present embodiment is configured to use a radial type c-MUT for obtaining a contour image, and a live organization cross-section image, of an endo cavity wall; an extraneous vibration component such as a standing wave, however, can be removed by adopting a convex type or linear type. Also, the present embodiment is configured to use an optical sensor for detecting a state of the ultrasonic transducer; the detection of whether or not the ultrasonic transducer contacting with an endo cavity wall, however, is possible by using a pressure sensor, for example. And, the present embodiment is configured to transmit an ultrasound within an ultrasonic anechoic cell for sensing only an extraneous vibration component such as a standing wave; it may be, however, an anechoic environment in which the ultrasound is not reflected.

Third Embodiment

While the second embodiment is configured to detect whether or not the ultrasonic transducer contacts with an endo cavity wall by using an optical sensor, the present third embodiment describes the case of detecting whether or not an ultrasonic transducer contacts with an endo cavity wall by a difference of a received ultrasonic frequency.

Figure 23:
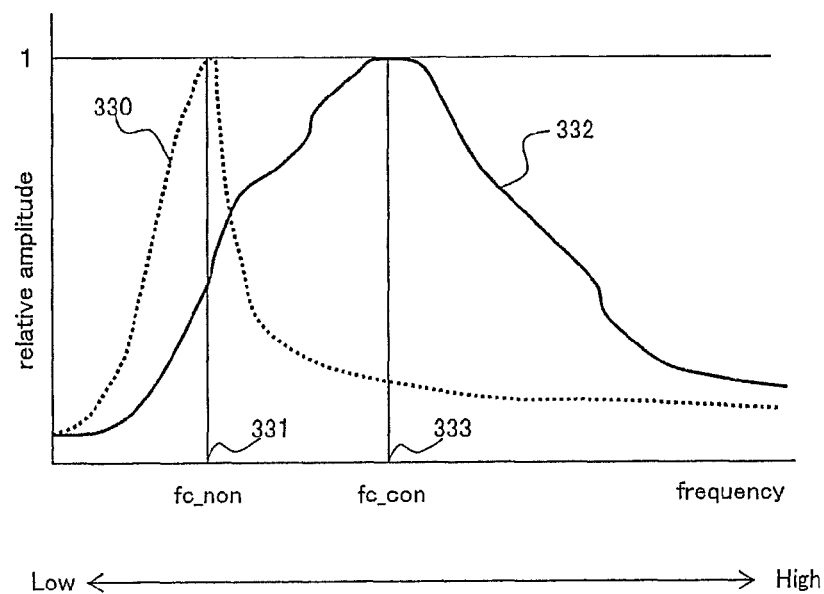
FIG. 23 is a diagram showing a frequency characteristic when a target object is contacting and not contacting with an ultrasonic transducer according to a third embodiment.

FIG. 23 is a graph showing a frequency characteristic when a target object is contacting or not contacting with an ultrasonic transducer according to the present embodiment. The vertical axis of the graph shows a relative amplitude (i.e., values divided by a maximum value of them in the vertical axis (i.e., normalized), while the horizontal axis shows frequencies.

The numerical 330 shows a frequency characteristic in a state of the ultrasonic transducer not in contact with an object. The 331 shows a peak frequency (fc_non) in a state of the ultrasonic transducer not in contact with an object (i.e., the curve 330). The 332 is a frequency characteristic in a state of the ultrasonic transducer in contact with an object. The 333 shows a peak frequency (fc_con) in a state of the ultrasonic transducer in contact with an object (i.e., the curve 332).

There is a large difference in the frequency characteristic of the ultrasound transmitted between the ultrasonic transducer being in contact and not in contact with an object, that is, an organ wall of the endo cavity according to the graph. The FIG. 20 of the non-patent document 2, for example, notes such a change of the frequency characteristic between the contact and noncontact. The non-patent document 2 notes that a change in a frequency characteristic between the contact and noncontact is caused by: (1) difference in an acoustic impedance of an acoustic load (i.e., water and air) from the view point of a membrane, (2) an internal pressure of a cavity located behind the membrane is different due to an acoustic load (i.e., water and air), and (3) a transmission of a high frequency ultrasound into the air is difficult.

Therefore, a provision of a threshold value between the fc_con and fc_non enables a discernment of which state (i.e., the curve 330 or curve 332) the ultrasonic transducer is in by using the threshold value as a border.

Figure 24:
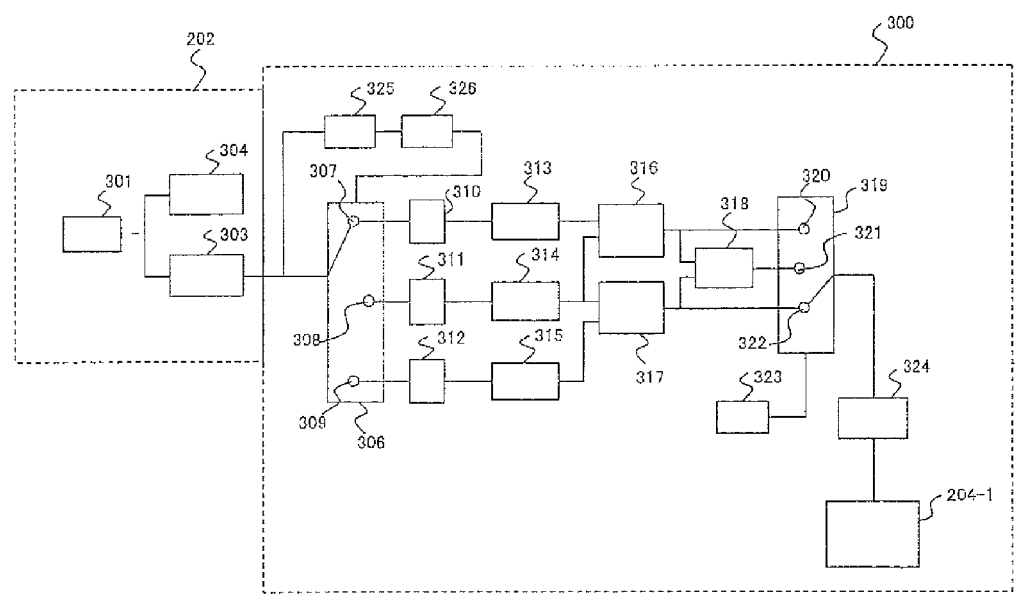
FIG. 24 is a diagram showing an outline of an internal comprisal of an endo cavity ultrasonic diagnosis system according to the third embodiment.

FIG. 24 shows an outline of an internal comprisal of an endo cavity ultrasonic diagnosis system according to the present embodiment. FIG. 24 shows a configuration of removing the optical sensor 302 and signal process circuit for optical sensor 305 and adding a low pass filter 325 and a wave detector 326 from FIG. 22.

A signal based on charge information detected by the charge amplifier 303 is input to the low pass filter 325 which is for passing a signal of lower frequencies than a preset threshold. Therefore, it is possible to discern that a signal passing the low pass filter is a reception signal in the state of the ultrasonic transducer not contacting with an object, while a signal unable to pass it is a reception signal in the state of the ultrasonic transducer contacting with the object.

The wave detector 326 is for detecting a wave of a signal (i.e., an alternate current signal) output from the low pass filter 325 and converting it into a direct current (DC) signal for driving the switch circuit 306. In the case of an ultrasonic reception signal being a low frequency, it passes the low pass filter 325 and the ultrasonic reception signal is input to the wave detector 326 and subjected to an AC/DC conversion. In the case of the ultrasonic reception signal being a high frequency, it is cut by the low pass filter 325 and therefore the ultrasonic reception signal is not input to the wave detector 326, hence no output therefrom. Meanwhile, a reception signal within the ultrasonic anechoic chamber 270 is not observed other than a low level noise, and therefore no output comes out of the wave detector 326. Therefore, an output from the wave detector 326 is zero at the time of detecting a calibration signal (refer to FIG. 20), is a high level output at the time of inserting into a lumen (refer to FIG. 21A), and is a low level output at the time of being fixed in contact (refer to FIG. 21B). The switches of the switch circuit 306 is changed over from the SW1 (307) to SW2 (308) to SW3 (309) in accordance with the difference of the wave detection output, and a reception signal in each of the state is transmitted to the AD converters 310, 311 and 312. The operations thereafter are the same as those of the second embodiment.

By the above operations, the discernment of the difference in frequency characteristic makes it possible to detect whether the ultrasonic transducer is on the outside of a human body, or in the inside of an endo cavity and not in contact with an inner wall, or in contact therewith, thereby enabling a detection of the state of the ultrasonic transducer.

Fourth Embodiment

The present fourth embodiment describes a variation of a signal process based on an ultrasonic reception signal obtained in each state.

FIG. 25 shows an arithmetic operation control circuit 350 for performing a signal process of a plurality of patterns according to the present embodiment. The arithmetic operation control circuit 350 is a group of circuits corresponding to the arithmetic operation process circuits (316, 317 and 318) and switch circuit 319 which are shown in FIG. 22.

The arithmetic operation control circuit 350 comprises distributors 351, 352 and 353, arithmetic operation process circuits 354, 355, 356, 357, 358 and 359, and a switch circuit 361. The distributors 351, 352 and 353 are for distributing signals output from the respective storage apparatuses 313, 314 and 315 to the respective arithmetic operation process circuits. The arithmetic operation process circuits 353 through 359 are for calculating a correlation, difference or sum of the input two reception signals.

The second or third embodiments is configured in a manner that a switch control signal 341 output from the signal process circuit for optical sensor 305 (refer to FIG. 22) or wave detector (refer to FIG. 24) is input to the switch circuit 306, a switch is changed over based on the information of the switch control signal 341.

Then, a signal (i.e., a reception signal 340) based on the charge information detected by the charge amplifier 303 is input to either one of the AD converter 310, 311 or 312 based on a changeover destination of the switch circuit 306. The AD converter 310, 311 or 312 converts the input analog signal into a digital signal. The converted reception signal 340 is input to, and stored in, the storage apparatus 313, 314 or 315 corresponding to the converter 310, 311 or 312.

Then, an operator uses the operation unit 323 for selecting as to which aspect of the reception signal is to be displayed, prompting an output of a switch control signal 345 from the operation unit 323 to be input to a switch circuit 361. Either of the selection terminals 361a, 361b, 361c, 361d, 361e, 361f, 361g, 361h or 361i is turned on in the switch circuit 361 based on the switch control signal 345, resulting in operating an arithmetic operation process circuit connected to the turned-On selection terminal.

Meanwhile, a control signal for memory device 342, 343 or 344 is generated based on the signal from the operation unit 323. The storage apparatus 313, receiving the control signal for memory device 342, outputs the stored reception signal (named as "S1" hereinafter) of the state 1 to the distributor 351. The storage apparatus 314, receiving the control signal for memory device 343, outputs the stored reception signal (named as "S2" hereinafter) of the state 2 to the distributor 352. The storage apparatus 315, receiving the control signal for memory device 344, outputs the stored reception signal (named as "S3" hereinafter) of the state 3 to the distributor 353.

Then, the signal output from each of the storage units 313 through 315 is processed by an arithmetic operation by the arithmetic operation process circuit, output as an arithmetic operation process signal 346 by way of the switch circuit 361, and input to the image converter 324. The operations thereafter are the same as those of the second embodiment.

The next description is on each arithmetic operation in the case of each of the selection terminals 361 being turned On.

[Case 1] In the case of the selection terminal 361a being turned On, the signal S1 output from the distributor 351 is output as an arithmetic operation process signal 346.

[Case 2] In the case of the selection terminal 361d being turned On, the signal S2 output from the distributor 352 is output as an arithmetic operation process signal 346.

[Case 3] In the case of the selection terminal 361i being turned On, the signal S3 output from the distributor 353 is output as an arithmetic operation process signal 346.

[Case 4] In the case of the selection terminal 361b being turned On, the signals S1 and S2 output from the distributors 351 and 352 are input to an arithmetic operation process circuit 354. The arithmetic operation process circuit 354 performs an arithmetic operation of S4=S2−S1 for generating a signal S4. And the generated signal S4 is output as an arithmetic operation process signal 346.

[Case 5] In the case of the selection terminal 361f being turned On, the signals S1 and S3 output from the distributors 351 and 353 are input to an arithmetic operation process circuit 355 which then performs an arithmetic operation of S5=S3−S1 for generating a signal S5. And the generated signal S5 is output as an arithmetic operation process signal 346.

[Case 6] In the case of the selection terminal 361h being turned On, the signals S2 and S3 output from the distributors 352 and 353 are input to an arithmetic operation process circuit 356 which then performs an arithmetic operation of S6=S3−S1 for generating a signal S6. And the generated signal S6 is output as an arithmetic operation process signal 346.

[Case 7] In the case of the selection terminal 361c being turned On, the signals S4 and S5 generated at the arithmetic operation process circuits 354 and 355 are input to an arithmetic operation process circuit 357 which then performs an arithmetic operation of S7=S4+S5 for generating a signal S7. And the generated signal S7 is output as an arithmetic operation process signal 346.

[Case 8] In the case of the selection terminal 361e being turned On, the signals S5 and S6 generated at the arithmetic operation process circuits 355 and 366 are input to an arithmetic operation process circuit 358 which then performs an arithmetic operation of S8=S5+S6 for generating a signal S8. And the generated signal S8 is output as an arithmetic operation process signal 346.

[Case 9] In the case of the selection terminal 361g being turned On, the signals S4 and S6 generated at the arithmetic operation process circuits 354 and 356 are input to an arithmetic operation process circuit 359 which then performs an arithmetic operation of S9=S4+S6 for generating a signal S9. And the generated signal S9 is output as an arithmetic operation process signal 346.

Each arithmetic operation process is described in detail at this point. The alpha-numerical S1 is noise data related to measurement data (i.e., a noise or fluctuation stemming from a transducer (including a drive signal) occurring in association of an ultrasound transmission) at an ultrasonic anechoic cell 270 shown in FIG. 20 (i.e., the state 1) for example, and the noise stemming from the transducer includes a crosstalk vibrational wave related to an in-plane transverse wave propagation unique to the c-MUT and a standing wave.

The S2 is reception ultrasound data in the process of inserting the ultrasonic transducer into an endo cavity as shown in FIG. 21A (i.e., the state 2) and it corresponds to a surface reflection signal from a luminal wall of an endo cavity by using a noncontact aerial ultrasound. This signal also includes a noise signal related to a noise and fluctuation stemming from the transducer. Therefore, the arithmetic operation of "S4=S2−S1" can remove the noise signal.

Next, the S3 is data including deep diagnosis measurement information in the case of the transducer fixing and in contact with a luminal wall surface as shown in FIG. 21B (i.e., the state 3) and it corresponds to a deep reflection signal. This signal includes signal components of the S1 and S2. In this case the S1 signal is a noise signal, needing to be removed and therefore the arithmetic operation and therefore the arithmetic operation of "S5=S3−S1" is performed.

Meanwhile, since the S2 signal includes a noise signal, there is a case of an arithmetic operation of "S6=S3−S2" being suitable; it results in, however, removing also a surface reflection signal of a luminal wall included in the S3 simultaneously. Such a signal process has a shortfall of losing information on an organization of a luminal wall surface of an endo cavity on one hand, while it has an advantage of providing a better view of a deep diagnosis image as a result of deleting the information on the organization of the luminal wall surface on the other hand. As such, whether using "S5=S3−S1" or "S6=S3−S2" is a discretion of the operator. This method leads to improving a freedom of diagnosis.

Note that the "S7=S4+S5", being a result of adding a surface reflection signal from a luminal wall with a noise being removed and a deep diagnosis signal with a noise being removed, enables a uniform diagnosis from the surface to deep part. Also the "S8=S5+S6" and "S9=S4+S6" make it possible to obtain images taking advantage of benefits of the respective signals.

Incidentally, there is a case of the operator being interested in knowing "how the original signal was", and the capability of detecting by selecting single signals S1, S2 and S3 is provided by the equipment of the switch circuit 361. Although the present embodiment does not describe a signal process after the control signal for memory device 343 in detail, it enables a display of a separate window in a monitor screen, for example, that is a display apparatus.

Also, the present embodiment is configured to calculate the difference between the input two signals at the arithmetic operation process circuits 354, 355 and 356; a correlation function (e.g., a cross-correlation and an autocorrelation), however, may be used as in the case of the second embodiment.

Furthermore, the c-MUT is responsive to a Doppler signal control and harmonic imaging, and the ultrasonic diagnosis system of the present invention is applicable thereto.

As described above, various pattern of signal process can be carried out based on an ultrasound reception signal obtained in each state selected by the operator. This makes it possible to have a generated ultrasonic diagnosis image comprise a characteristic corresponding to the signal process, thereby enabling a multiple aspects of diagnoses.

The present invention eliminates a necessity of decreasing a ratio of an area size of cell zone to the entirety for a c-MUT featured with trenches on both ends of an element, thereby eliminating a possibility of decreasing an output of the ultrasonic transducer.

Also, the present invention enables a transmission and reception of an ultrasound in the state of an ultrasonic transducer contacting with an endo cavity wall and not contacting therewith, and also a transmission of the reception signal of the received ultrasound in each state to a corresponding channel by detecting the state of the ultrasonic transducer.

Moreover, the present invention enables a buildup of an ultrasonic diagnosis image related to a contour while inserting an ultrasonic endoscopic scope equipped with a same c-MUT regardless of it contacting or not contacting with an endo cavity wall, and also a buildup of an ultrasonic diagnosis image related to a cross-sectional image when reaching at a diagnosis region and being fixed in contact therewith. And, a noise component caused by a standing wave is removed from the thusly buildup ultrasonic diagnosis images.

The invention claimed is:

1. A noise elimination apparatus for eliminating a noise component from sensed information sensed by a capacitive ultrasonic transducer (c-MUT) used for an endo cavity ultrasonic endoscopic diagnosis system comprising an ultrasonic endoscopic scope equipped with the c-MUT for transmitting and receiving an ultrasound, comprising:

a first storage device configured to store first sensed information sensed by making the c-MUT transmit an ultrasound under a condition of the ultrasound not reflecting;

a sensor signal analysis circuit configured to obtain a sensor signal from a sensor provided approximately near the capacitive ultrasonic transducer, to analyze the sensor signal, and to determine whether the capacitive ultrasonic transducer is in a state of being inside a cavity of a body and yet not touching an inside wall thereof;

a receiver device configured to receive second sensed information when the sensor signal analysis circuit determines that the capacitive ultrasonic transducer is in a state of being inside of the cavity and yet not touching the inside wall thereof, the second sensed information being sensed by the capacitive ultrasonic transducer transmitting and receiving the ultrasound in the determined state;

a second storage device configured to store the received second sensed information; and an arithmetic operation processing circuit configured to calculate a correlation or difference between the second sensed information and first sensed information.

2. A noise elimination apparatus for eliminating a noise component from sensed information sensed by a capacitive ultrasonic transducer (c-MUT) used for an endo cavity ultrasonic endoscopic diagnosis system comprising an ultrasonic endoscopic scope equipped with the c-MUT for transmitting and receiving an ultrasound, comprising:

a first storage device configured to store first sensed information sensed by making the c-MUT transmit an ultrasound under a condition of the ultrasound not reflecting;

a sensor signal analysis circuit configured to obtain a sensor signal from a sensor provided approximately near the capacitive ultrasonic transducer, to analyze the sensor signal, and to determine whether the capacitive ultrasonic transducer is in a state of touching an inside wall of a cavity of a body;

a receiver device configured to receive third sensed information when the sensor signal analysis circuit determines that the capacitive ultrasonic transducer is in a state of touching the inside wall of the cavity, the third sensed information being sensed by the capacitive ultrasonic transducer transmitting and receiving the ultrasound in the determined state;

a third storage device configured to store third sensed information; and an arithmetic operation processing circuit configured to calculate a correlation or difference between the third sensed information and first sensed information.

* * * * *